(12) United States Patent
Bonuttti

(10) Patent No.: US 9,474,676 B2
(45) Date of Patent: Oct. 25, 2016

(54) ACOUSTIC THERAPY DEVICE

(71) Applicant: P Tech, LLC, Effingham, IL (US)

(72) Inventor: Peter M Bonuttti, Delray Beach, FL (US)

(73) Assignee: P Tech, LLC, Effingham, IL (US)

( * ) Notice: Subject to any disclaimer, the term of this patent is extended or adjusted under 35 U.S.C. 154(b) by 0 days.

(21) Appl. No.: 14/321,420

(22) Filed: Jul. 1, 2014

(65) Prior Publication Data

US 2014/0336545 A1    Nov. 13, 2014

Related U.S. Application Data

(63) Continuation of application No. 14/054,301, filed on Oct. 15, 2013, now abandoned, which is a continuation of application No. 10/945,331, filed on Sep. 20, 2004, now Pat. No. 8,750,983.

(51) Int. Cl.

| | | |
|---|---|---|
| *A61N 7/00* | (2006.01) | |
| *A61H 1/00* | (2006.01) | |
| *A61B 17/22* | (2006.01) | |
| *A61H 23/00* | (2006.01) | |
| *A61N 1/378* | (2006.01) | |
| *A61N 1/40* | (2006.01) | |
| *A61N 2/02* | (2006.01) | |
| *A61B 17/00* | (2006.01) | |

(52) U.S. Cl.
CPC .......... *A61H 1/008* (2013.01); *A61B 17/22012* (2013.01); *A61H 23/00* (2013.01); *A61N 7/00* (2013.01); *A61B 2017/00022* (2013.01); *A61F 2250/0001* (2013.01); *A61H 2023/002* (2013.01); *A61H 2201/02* (2013.01); *A61H 2201/10* (2013.01); *A61N 1/3787* (2013.01); *A61N 1/40* (2013.01); *A61N 2/02* (2013.01)

(58) Field of Classification Search
CPC ........... A61H 2209/00; A61H 9/0078; A61H 1/008; A61H 23/00; A61H 2201/10; A61N 7/00; A61N 2007/0047
USPC ........................................ 607/100, 101, 103
See application file for complete search history.

(56) References Cited

U.S. PATENT DOCUMENTS

| | | | |
|---|---|---|---|
| 3,279,996 A | 10/1966 | Long | |
| 3,948,254 A | 4/1976 | Zaffaroni | |
| 4,200,098 A | 4/1980 | Ayer | |
| 4,211,289 A * | 7/1980 | Klein | ................. A61B 5/02233 |
| | | | 172/686 |
| 4,351,337 A | 9/1982 | Sidman | |

(Continued)

FOREIGN PATENT DOCUMENTS

| | | |
|---|---|---|
| CA | 2580784 | 3/2006 |
| DE | 10209494 | 11/2002 |

OTHER PUBLICATIONS

Calcific Tendinitis—Wikipedia Encyclopedia—en.wikipedia.org—pp. 1-3, Retrieved Sep. 29, 2009.

(Continued)

*Primary Examiner* — Kaitlyn Smith

(57) ABSTRACT

The present disclosure provides a system for treatment of Deep Vein Thrombosis. The system includes an appliance configured to secure to a portion of a body of a user and a plurality of energy units, coupled to the appliance, that provide energy inside the body of the user to at least one of break-up thrombin or a clot formation and increase vascular flow.

5 Claims, 12 Drawing Sheets

(56) References Cited

U.S. PATENT DOCUMENTS

| | | | |
|---|---|---|---|
| 4,666,704 A | 5/1987 | Shalati | |
| 4,719,919 A | 1/1988 | Marchosky et al. | |
| 4,871,542 A | 10/1989 | Vilhardt | |
| 4,905,671 A | 3/1990 | Senge | |
| 4,926,859 A | 5/1990 | Field | |
| 4,955,385 A | 9/1990 | Kvalo | |
| 5,016,615 A | 5/1991 | Driller | |
| 5,022,387 A * | 6/1991 | Hasty | 601/152 |
| 5,158,071 A | 10/1992 | Umemura | |
| 5,211,160 A * | 5/1993 | Talish | A61B 8/0875 601/2 |
| 5,267,985 A | 12/1993 | Shimada | |
| 5,399,158 A * | 3/1995 | Lauer et al. | 604/22 |
| 5,520,612 A | 5/1996 | Winder | |
| 5,524,624 A | 6/1996 | Tepper | |
| 5,749,909 A | 5/1998 | Schroeppel | |
| 5,755,746 A * | 5/1998 | Lifshey | A61B 6/12 600/407 |
| 5,836,896 A | 11/1998 | Rosenchein | |
| 5,843,007 A * | 12/1998 | McEwen | A61H 9/0078 601/149 |
| 5,928,145 A | 7/1999 | Ocali | |
| 5,947,893 A | 9/1999 | Agrawal | |
| 5,967,986 A | 10/1999 | Cimoshowski | |
| 5,972,029 A | 10/1999 | Fuisz | |
| 6,022,554 A | 2/2000 | Lee | |
| 6,053,873 A | 4/2000 | Govari | |
| 6,069,295 A | 5/2000 | Leitao | |
| 6,083,232 A | 7/2000 | Cox | |
| 6,179,817 B1 | 1/2001 | Zhong | |
| 6,190,591 B1 | 2/2001 | Van Lengerrich | |
| 6,207,218 B1 | 3/2001 | Layrolle | |
| 6,238,421 B1 | 5/2001 | Gunther | |
| 6,248,363 B1 | 6/2001 | Patel | |
| 6,258,121 B1 | 7/2001 | Yang | |
| 6,282,736 B1 * | 9/2001 | Hand et al. | 5/608 |
| 6,361,554 B1 | 3/2002 | Brisken | |
| 6,398,734 B1 | 6/2002 | Cimochowshi | |
| 6,398,777 B1 * | 6/2002 | Navarro | A61N 5/0601 128/898 |
| 6,413,215 B1 | 7/2002 | Wu | |
| 6,428,491 B1 | 8/2002 | Weiss | |
| 6,433,464 B2 | 8/2002 | Jones | |
| 6,436,061 B1 * | 8/2002 | Costantino | A61N 7/00 600/439 |
| 6,444,217 B1 | 9/2002 | Kwok et al. | |
| 6,454,775 B1 * | 9/2002 | Demarais et al. | 606/128 |
| 6,477,424 B1 | 11/2002 | Thompson | |
| 6,524,333 B1 | 2/2003 | Claren | |
| 6,544,185 B2 | 4/2003 | Montegrande | |
| 6,572,614 B1 | 6/2003 | Ellman | |
| 6,585,762 B1 | 7/2003 | Stanish | |
| 6,585,763 B1 | 7/2003 | Keilman | |
| 6,585,764 B2 | 7/2003 | Wright | |
| 6,586,133 B1 | 7/2003 | Teeters | |
| 6,626,940 B2 | 9/2003 | Crowley | |
| 6,656,162 B2 | 12/2003 | Santini | |
| 6,702,850 B1 | 3/2004 | Byun | |
| 6,709,427 B1 | 3/2004 | Nash | |
| 6,730,064 B2 | 5/2004 | Ragheb | |
| 6,733,451 B2 | 5/2004 | Rabiner | |
| 6,736,842 B2 | 5/2004 | Healy | |
| 6,786,904 B2 | 9/2004 | Doscher | |
| 6,790,456 B2 | 9/2004 | Vogel | |
| 6,908,448 B2 | 6/2005 | Redding | |
| 7,077,859 B2 | 7/2006 | Sirhan | |
| 7,160,316 B2 * | 1/2007 | Hamilton et al. | 607/111 |
| 7,182,726 B2 | 2/2007 | Williams | |
| 7,207,959 B1 * | 4/2007 | Chandran | A61H 9/0078 601/149 |
| 7,223,227 B2 | 5/2007 | Pflueger | |
| 7,462,158 B2 * | 12/2008 | Mor | 601/46 |
| 7,522,955 B2 | 4/2009 | Rontal | |
| 7,655,243 B2 | 2/2010 | Deem | |
| 7,819,826 B2 | 10/2010 | Diederich | |
| 7,967,820 B2 | 6/2011 | Bonutti | |
| 8,033,977 B2 | 10/2011 | Hainfeld | |
| 8,083,707 B2 | 12/2011 | Tosaya | |
| 8,105,817 B2 | 1/2012 | Deem | |
| 8,280,484 B2 | 10/2012 | Boyden | |
| 8,414,509 B2 | 4/2013 | Diederich | |
| 8,454,542 B2 * | 6/2013 | Hirata et al. | 601/150 |
| 8,485,995 B1 * | 7/2013 | Maxon-Maldonado | 601/15 |
| 8,491,572 B2 | 7/2013 | Martinson | |
| 2001/0000262 A1 * | 4/2001 | McEwen | A61H 9/0078 601/11 |
| 2001/0018072 A1 | 8/2001 | Unger | |
| 2002/0040184 A1 * | 4/2002 | Brown et al. | 600/407 |
| 2002/0055702 A1 | 5/2002 | Atala et al. | |
| 2002/0082529 A1 * | 6/2002 | Suorsa et al. | 601/2 |
| 2002/0128704 A1 | 9/2002 | Daum | |
| 2002/0173796 A1 | 11/2002 | Cragg | |
| 2002/0193874 A1 | 12/2002 | Crowley | |
| 2003/0069528 A1 * | 4/2003 | Herz | A61H 9/0078 601/152 |
| 2003/0083646 A1 | 5/2003 | Sirhan | |
| 2003/0088274 A1 | 5/2003 | Gliner | |
| 2003/0092667 A1 | 5/2003 | Tachibana et al. | |
| 2003/0158557 A1 | 8/2003 | Cragg | |
| 2003/0225331 A1 | 12/2003 | Diederich | |
| 2004/0013703 A1 | 1/2004 | Ralph | |
| 2004/0039441 A1 | 2/2004 | Rowland | |
| 2004/0044298 A1 | 3/2004 | Kawabata | |
| 2004/0077978 A1 * | 4/2004 | Nelson et al. | 601/70 |
| 2004/0158317 A1 | 8/2004 | Brisken | |
| 2004/0230117 A1 | 11/2004 | Tosaya | |
| 2004/0236268 A1 | 11/2004 | Mitragotri | |
| 2005/0038377 A1 | 2/2005 | Redding | |
| 2005/0143797 A1 * | 6/2005 | Parish et al. | 607/104 |
| 2005/0256554 A1 * | 11/2005 | Malak | A61N 5/0616 607/88 |
| 2005/0283110 A1 | 12/2005 | Atala | |
| 2006/0016012 A1 * | 1/2006 | Liu | 5/651 |
| 2006/0036203 A1 * | 2/2006 | Ouchene | A61H 9/0078 601/151 |
| 2006/0047283 A1 | 3/2006 | Evans | |
| 2006/0069343 A1 | 3/2006 | Rontal | |
| 2006/0106273 A1 | 5/2006 | Apple | |
| 2006/0122544 A1 * | 6/2006 | Ciluffo | A41D 13/0015 601/15 |
| 2006/0287733 A1 | 12/2006 | Bonutti | |
| 2007/0033696 A1 * | 2/2007 | Sellier | A41D 13/0017 2/69 |
| 2007/0078290 A1 | 4/2007 | Esenaliev | |
| 2007/0088346 A1 * | 4/2007 | Mirizzi | A61N 7/02 606/27 |
| 2007/0141106 A1 | 6/2007 | Bonutti | |
| 2007/0197853 A1 | 8/2007 | Pflueger | |
| 2007/0213645 A1 | 9/2007 | Zumeris | |
| 2007/0293909 A1 | 12/2007 | Cowan | |
| 2008/0004548 A1 * | 1/2008 | Oshmyansky | A61H 9/0078 601/2 |
| 2008/0021369 A1 | 1/2008 | Deem | |
| 2008/0021474 A1 | 1/2008 | BOnutti | |
| 2008/0021531 A1 * | 1/2008 | Kane et al. | 607/111 |
| 2008/0039845 A1 | 2/2008 | Bonutti | |
| 2008/0051680 A1 | 2/2008 | Luebcke | |
| 2008/0058783 A1 | 3/2008 | Altshuler | |
| 2008/0058911 A1 * | 3/2008 | Parish et al. | 607/104 |
| 2008/0064992 A1 * | 3/2008 | Stewart et al. | 601/7 |
| 2008/0119845 A1 | 5/2008 | Stone | |
| 2008/0132816 A1 * | 6/2008 | Kane et al. | 601/152 |
| 2008/0132976 A1 * | 6/2008 | Kane et al. | 607/104 |
| 2008/0140026 A1 | 6/2008 | Silwa | |
| 2008/0161884 A1 * | 7/2008 | Chandler | A61N 1/0468 607/50 |
| 2008/0234535 A1 * | 9/2008 | Malak | A61N 5/06 600/15 |
| 2008/0312562 A1 * | 12/2008 | Routh | A61B 8/06 601/2 |
| 2008/0319359 A1 * | 12/2008 | Moomiaie-Qajar | A61H 11/00 601/152 |
| 2009/0069731 A1 * | 3/2009 | Parish et al. | 601/150 |
| 2009/0163964 A1 | 6/2009 | Boyden | |

(56) References Cited

U.S. PATENT DOCUMENTS

| | | | |
|---|---|---|---|
| 2009/0163965 A1 | 6/2009 | Boyden | |
| 2009/0163977 A1 | 6/2009 | Boyden | |
| 2009/0171263 A1 | 7/2009 | Boyden | |
| 2009/0177139 A1 | 7/2009 | Boyden | |
| 2009/0177184 A1* | 7/2009 | Christensen et al. | 604/506 |
| 2009/0177254 A1 | 7/2009 | Boyden | |
| 2009/0209830 A1* | 8/2009 | Nagle | A43B 7/147 600/301 |
| 2009/0254008 A1* | 10/2009 | Shields, Jr. | A61N 7/00 601/3 |
| 2009/0312816 A1 | 12/2009 | Gross | |
| 2010/0042027 A1* | 2/2010 | Hirata et al. | 601/151 |
| 2010/0049177 A1 | 2/2010 | Boone | |
| 2010/0057149 A1* | 3/2010 | Fahey | A61H 11/00 607/3 |
| 2010/0087775 A1 | 4/2010 | Deem | |
| 2010/0145412 A1 | 6/2010 | Boyden | |
| 2010/0174346 A1 | 7/2010 | Boyden | |
| 2010/0210982 A1* | 8/2010 | Balachandran et al. | 601/152 |
| 2010/0292632 A1 | 11/2010 | Mulvihill | |
| 2011/0034832 A1 | 2/2011 | Cioanta | |
| 2011/0040212 A1 | 2/2011 | Dietz | |
| 2011/0040213 A1 | 2/2011 | Dietz | |
| 2011/0071426 A1* | 3/2011 | Marasco | A61B 19/38 600/562 |
| 2011/0112352 A1* | 5/2011 | Pilla | A61N 1/40 600/14 |
| 2011/0152789 A1 | 6/2011 | Dacey | |
| 2011/0152790 A1 | 6/2011 | Dacey | |
| 2011/0166621 A1 | 7/2011 | Cowan | |
| 2011/0172749 A1* | 7/2011 | Christensen et al. | 607/104 |
| 2011/0207989 A1* | 8/2011 | Pilla | A61N 1/40 600/14 |
| 2011/0208021 A1 | 8/2011 | Goodall | |
| 2011/0208023 A1 | 8/2011 | Goodall | |
| 2011/0208026 A1 | 8/2011 | Goodall | |
| 2011/0245734 A1 | 10/2011 | Wagner | |
| 2011/0257565 A1* | 10/2011 | Wilford et al. | 601/18 |
| 2011/0264032 A1 | 10/2011 | Rontal | |
| 2011/0269693 A1 | 11/2011 | Luebcke | |
| 2011/0275912 A1 | 11/2011 | Boyden | |
| 2011/0295088 A1 | 12/2011 | Boyden | |
| 2011/0295089 A1 | 12/2011 | Boyden | |
| 2011/0295090 A1 | 12/2011 | Boyden | |
| 2012/0010481 A1 | 1/2012 | Goodall | |
| 2012/0041285 A1 | 2/2012 | Goodall | |
| 2012/0041286 A1 | 2/2012 | Goodall | |
| 2012/0041287 A1 | 2/2012 | Goodall | |
| 2012/0165800 A1 | 6/2012 | Keeney | |
| 2012/0209090 A1 | 8/2012 | Goodall | |
| 2012/0232447 A1* | 9/2012 | Gordon et al. | 601/151 |
| 2012/0238936 A1 | 9/2012 | Hyde | |
| 2013/0012755 A1 | 1/2013 | Slayton | |
| 2013/0019374 A1* | 1/2013 | Schwartz | 2/69 |
| 2013/0030331 A1* | 1/2013 | Quisenberry et al. | 601/18 |
| 2013/0046216 A1* | 2/2013 | O'Keefe et al. | 601/149 |
| 2013/0060147 A1* | 3/2013 | Welch | A61B 5/02208 600/479 |
| 2013/0066426 A1 | 3/2013 | Martinson | |
| 2013/0131575 A1 | 5/2013 | Dacey | |
| 2013/0245519 A1* | 9/2013 | Edelman et al. | 601/152 |
| 2013/0253383 A1* | 9/2013 | Maxon-Maldonado | 601/15 |
| 2014/0012169 A1* | 1/2014 | Wilford et al. | 601/151 |
| 2014/0114117 A1* | 4/2014 | Naghavi | A61B 5/02233 600/13 |
| 2014/0249455 A1* | 9/2014 | Parish et al. | 601/22 |
| 2014/0276257 A1* | 9/2014 | Santa Maria | A61F 7/02 601/18 |
| 2014/0303425 A1* | 10/2014 | Pilla | A61N 2/006 600/14 |
| 2015/0018869 A1* | 1/2015 | Benz et al. | 606/203 |

OTHER PUBLICATIONS

Springer Milan—Springer Link—Journal Article Abstract, Title Extracorporeal Shock Wave Therapy for Chronic Calcifying Tendinitis of the Shoulder, Mar. 15, 2002, pp. 1-2, Retrieved Sep. 29, 2009.

www.advancedcoating.com/techinfo/thermal.html—Article, Thermal Properties, 4 pages, Jul. 25, 2009.

S. Sershen et al., Advanced Drug Delivery Reviews 54 (2002) 1225-1235—Implantable, polymeric systems for modulated drug delivery, 11 pages, © 2002 Elsevier Science B.V.

U.S. Appl. No. 60/273,850, filed Mar. 7, 2001, inventor Wolfgang Daum.

Written Opinion dated Apr. 12, 2007, for PCT/US2005/033731.

International Search Report for PCT/US2005/033731, published Mar. 30, 2006.

International Preliminary Report for PCT/US2005/033731, dated May 30, 2007.

Publication No. WO 2006/034306, published Mar. 30, 2006 for PCT/US2005/033731.

Supplementary Partial European Search Report for Application No. EP05798112, Publication No. EP17991361, published Jun. 27, 2007.

Annex to EPO Form 2004, Communication under Rule 71 (3) EPC, dated May 19, 2010, Intend to Grant, for Application No. EP05798112.

Canadian Office action for Application No. 2,580,784 dated Jan. 22, 2015, 3 pages.

Non-Final Office Action dated Sep. 10, 2013 relating to U.S. Appl. No. 10/945,331, 6 pgs.

Non-Final Office Action dated Jul. 31, 2012 relating to U.S. Appl. No. 10/945,331, 6 pgs.

Final Office Action dated Mar. 15, 2011 relating to U.S. Appl. No. 10/945,331, 6 pgs.

Final Office Action dated Jul. 22, 2010 relating to U.S. Appl. No. 10/945,331, 4 pgs.

Non-Final Office Action dated Dec. 14, 2009 relating to U.S. Appl. No. 10/945,331, 19 pgs.

Final Office Action dated Mar. 30, 2009 relating to U.S. Appl. No. 10/945,331, 19 pgs.

Non-Final Office Action dated May 7, 2008 relating to U.S. Appl. No. 10/945,331, 16 pgs.

Final Office Action dated Oct. 15, 2007 relating to U.S. Appl. No. 10/945,331, 16 pgs.

Non-Final Office Action dated Apr. 19, 2007 relating to U.S. Appl. No. 10/945,331, 11 pgs.

Non-Final Office Action dated Jan. 3, 2014 relating to U.S. Appl. No. 14/054,301, 13 pgs.

* cited by examiner

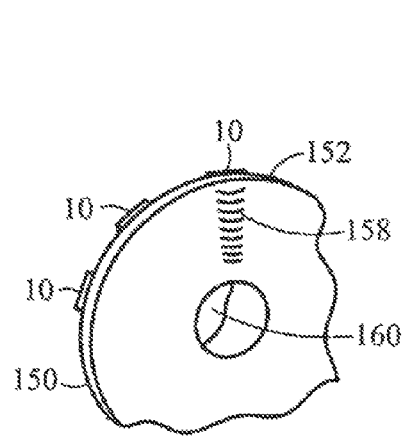
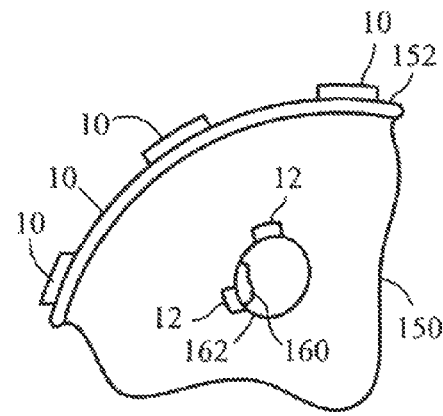
FIG. 22  FIG. 23
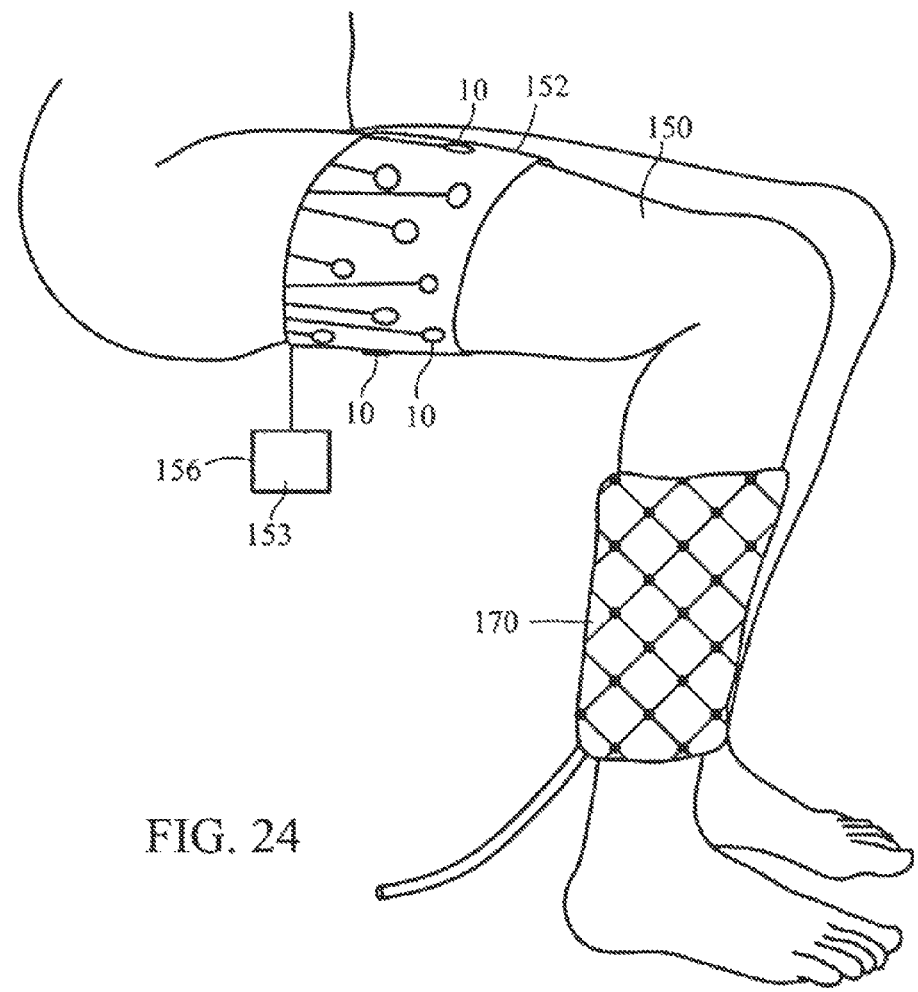
FIG. 24

ACOUSTIC THERAPY DEVICE

CROSS REFERENCE TO RELATED APPLICATIONS

This patent application is a continuation application of U.S. patent application Ser. No. 14/054,301 filed on Oct. 15, 2013, which is a continuation application of U.S. patent application Ser. No. 10/945,331, now U.S. Pat. No. 8,750, 983, filed Sep. 20, 2004. The content of the above-identified applications are herein incorporated by reference in their entirety.

FIELD

The present disclosure relates to an acoustic therapy device. More specifically, the present disclosure relates to a system for treatment of Deep Vein Thrombosis. The system includes an appliance configured to secure to a portion of a body of a user and a plurality of energy units coupled to the appliance that provide energy inside the body of the user to at least one of break-up thrombin or a clot formation and increase vascular flow.

BACKGROUND

In the 1970s, the technique of percutaneous transluminal coronary angioplasty (PTCA) was developed for the treatment of atherosclerosis. Atherosclerosis is the build-up of fatty deposits or plaque on the inner walls of a patient's arteries; these lesions decrease the effective size of the vessel lumen and limit blood flow through the vessel, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guided wire to a point where the sclerotic lesions limit blood flow through the coronary artery. The balloon is then inflated, compressing the lesions radially outward against the wall of the artery and substantially increasing the size of its internal lumen, to improve blood circulation through the artery.

Other procedures have subsequently been developed for the treatment of atherosclerosis. These procedures include applying an energy to a treatment site to break-up the fatty deposits or plaque on the inner walls of a patient's arteries. Such energies can include ultrasonic, microwave, radio frequency, cryogenic, optical laser, thermal, magnetic, pH, etc. Generally, in these procedures, a guide wire is inserted into the femoral artery and is passed through the aorta into the diseased coronary artery. A catheter having an energy transmission device attached to its distal end is advanced along the guided wire to a point where the sclerotic lesions limit blood flow through the coronary artery. Energy, directed from the energy transmission device, is applied to the inner walls of the artery breaking-up the fatty deposits or plaque. The removal of the fatty deposits or plaque subsequently increases the size of its internal lumen, to improve blood circulation through the artery. However, in many instances the accumulation of the fatty deposits or plaque is a recurring or chronic problem, requiring additional and recurring treatments.

In the 1980s, the technique of extracorporeal shockwave lithotripsy (ESWL) was developed for the management of renal and ureteral calculous disease. ESWL is a procedure in which renal and ureteral calculi (stones) are pulverized into smaller fragments by shockwaves. These small fragments then can pass spontaneously. This noninvasive approach allows patients to be rendered stone-free without surgical intervention or endoscopic procedures.

Traditionally, this was accomplished by placing the patient in a large water bath (e.g., the early-generation machine; Dornier HM3). In newer second-generation and third-generation devices, the large water bath has been changed to the use of small pools of water or water-filled cushions with a silicone membrane to provide air-free contact with the patient's skin. With the new designs, patients can be treated in a variety of positions to help in localization and to maximize the effect.

As these examples illustrate, therapeutic energy has been used for treatment purposes. Nevertheless, there remains a need for improved systems and methods for delivering, utilizing, and/or providing energy to a treatment site in a body.

SUMMARY

The present disclosure provides a minimally invasive therapeutic system for providing energy to a treatment site within the body of a patient. More specifically, an external power source is provided for transmitting energy non-invasively through the skin and body of a patient to a medical implant. The medical implant is surgically or percutaneously positioned at a treatment site and generally includes an energy focusing device. The energy focusing device is configured to receive the transmitted energy and direct therapeutic energy to the treatment site to fragment the particulate material.

The medical implant may further include a sensor assembly surgically positioned at the treatment site. The sensor assembly may monitor the treatment site for material build-up. Similarly, the sensor assembly may be activated by the energy transmitted by the external power source. The energy focusing device and sensor assembly may be activated by the same frequency energy signal. Optionally, the energy focusing device and sensor assembly may be activated by energy signals of different frequencies, wherein the external energy unit is configured to transmit energy signals of different frequencies.

In use, the medical implant is surgically positioned at a treatment site. The external energy unit is positioned on a skin portion of the body of a patient or adjacent thereto, proximal to the treatment site. The energy signal is non-invasively transmitted through the body of the patient to the medical implant. The sensor assembly may utilize the energy signal to provide information regarding the treatment site. Similarly, the energy focusing device focuses the energy signal into the treatment site to fragment the particulate material.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 22 depicts a partial cross section view of the sleeve of FIG. 20 on a limb of a patient;

FIG. 23 depicts a partial cross section view of the sleeve of FIG. 20 on a limb of a patient including another embodiment of an implantable medical device of the present disclosure;

FIG. 24 depicts a compressive sleeve for use with the sleeve of FIG. 20:

DETAILED DESCRIPTION

The present disclosure is directed to a system and method for non-invasively, or in combination with invasive techniques, providing therapeutic energy to a treatment site in a patient's body. More specifically, an external power source or external energy transmittal device is provided for transmitting energy non-invasively through the skin and body of a patient to a medical implant or energy focusing device implanted within a patient's body. The medical implant, positioned at a desired treatment site, is configured to receive the transmitted energy and provide therapeutic energy treatment to the treatment site.

Figure 1:
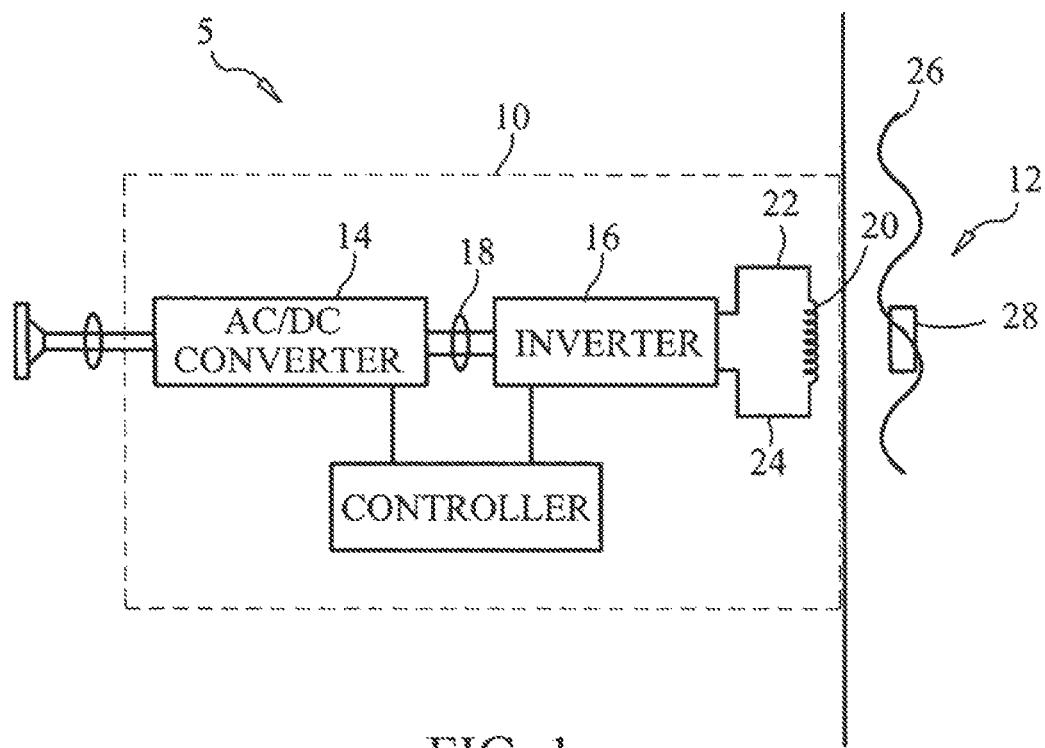
FIG. 1 depicts a schematic diagram of one embodiment of an energy system according to the present disclosure.

Referring now to the figures in which like reference numerals refer to like elements, an exemplary energy system 5 according to the present disclosure is shown in FIG. 1. Energy system 5 generally includes an external energy unit 10 and an implanted medical device 12. In one preferred embodiment, external energy unit 10 includes a conventional alternating current-to-direct current (AC/DC) converter 14 which is configured to receive 120 Volt AC electrical power from a conventional power source and convert the 120 Volt AC power to a lower magnitude DC voltage level. An inverter 16 receives the DC voltage via conductors 18 and generates an AC current that passes through external coil 20 via conductors 22 and 24. External coil 20 may be housed within the external unit 10 or housed separately. In operation, external coil 20 generates a changing magnetic field 26 which may be transmitted to the implanted medical device 12. The implanted medical device 12 includes an energy focusing device 28 configured to interact with magnetic field 26 to amplify the energy signal and/or create a convergent point shockwave, vibration, mechanical impulse or force, or other form of therapeutic energy.

The magnitude and extent of the therapeutic energy or forces created by device 28 is configured to be focused or directed toward an adjacent treatment site to break-up, dislodge, or otherwise fragment particulate material such as plaque, clotting, fatty deposits, etc., as the case may be. In this regard, the particulate material need not be biological material. For example, wear debris can be generated in conjunction with a prosthesis such as a total hip implant. Depending upon the implant material, this wear debris can be metallic, polymeric, and/or ceramic. Since the biological response is related to both the type of material and size of the particulate debris, it may be desirable to apply the therapeutic energy or forces so that the wear debris is fragmented to a given size range. Furthermore, the application of the energy or forces itself may be used to condition the biological response. For example, cells such as macrophages, known to be active in the response to wear debris, can be preferentially attracted or repelled from the site by device 28.

It is also envisioned by the present disclosure to use the therapeutic energy or forces to simply control or modulate fluid flow through a vessel. This is described in more detail below.

Figure 2:
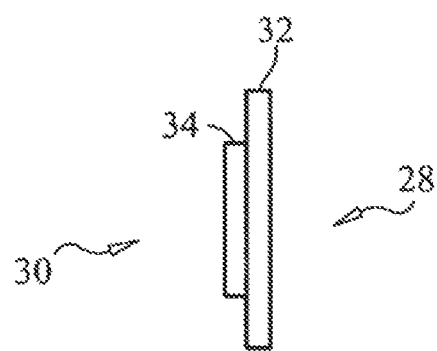
FIG. 2 depicts one embodiment of an energy focusing device according to the present disclosure.

Referring to FIG. 2, one exemplary embodiment is shown wherein energy focusing device 28 is a piezoelectric device 30 which generally includes a ferromagnetic plate 32 attached to a ceramic disk 34. In this embodiment, the alternating current that passes through external coil 20 generates a changing magnetic field 26 that interacts with piezoelectric device 30 to cause ferromagnetic plate 32 and ceramic disk 34 to vibrate, creating a convergent point shockwave. The frequency and magnitude of the mechanical vibrations of piezoelectric device 30 are proportional to the magnitude and frequency of the magnetic field 26.

The extent of vibration of piezoelectric device 30 depends, at least in part, on the physical placement of external coil 20 relative to the piezoelectric device 30. To maximize energy efficiency, the external coil 20 may be positioned such that a maximum number of lines of magnetic flux of magnetic field 26 cross the surface of the ferromagnetic plate 32. In this regard, external coil 20 may be optimally positioned on the skin directly over the site at which the implanted medical device 12 is located.

Figure 3:
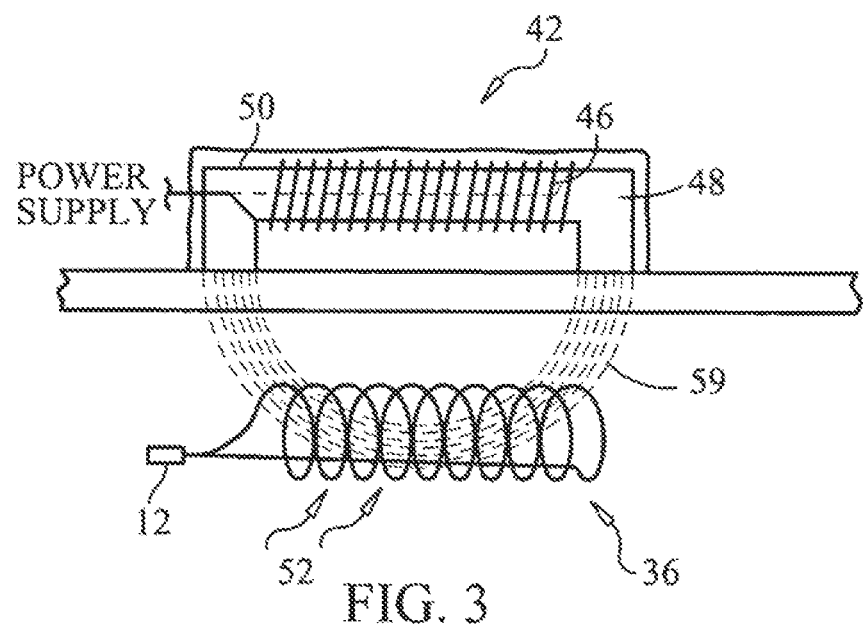
FIG. 3 depicts a schematic diagram of another embodiment of an energy system according to present disclosure including an internal RF coupling coil.

Referring to FIG. 3, another embodiment of an energy system is shown which includes a radio frequency (RF) coupling coil 36 implanted within a patient's body configured for receiving RF energy from an external RF transmitter 42. In operation, RF transmitter 42 may be disposed opposite the RF coupling coil 36 external to the patient and the RF coupling coil 36 may provide power to the implanted medical device 12. The external RF transmitter 42 includes a toroidal coil 46 disposed within the hollow center portion of a toroidal-shaped core 48. A housing 50 comprising an RF shield encloses much of the toroidal coil 46 and core 48. As noted above, when AC current passes through coil 46, lines of magnetic flux 54 intersect RF coupling coil 36 to provide electrical power for energizing the implanted medical device 12.

As shown in FIG. 3, the RF coupling coil 36 is a wound toroidal coil including a plurality of conductor coil loops 52. Although the drawing shows only a single coil 36 of spiral coil loops 52, it is contemplated that a plurality of coils of such coil loops may be used and that the spacing between coil loops 52 may be substantially closer than as shown.

In one embodiment, the implanted medical device 12 may additionally include a piezoelectric device 30. In operation, the alternating current passing through the RF coupling coil 36 causes ferromagnetic plate 32, and piezoelectric ceramic disk 34 to vibrate, creating a convergent point shockwave. The frequency and magnitude of the mechanical vibrations of piezoelectric device 30 are proportional to the alternating current passing through RF coupling coil 36.

Figure 4:
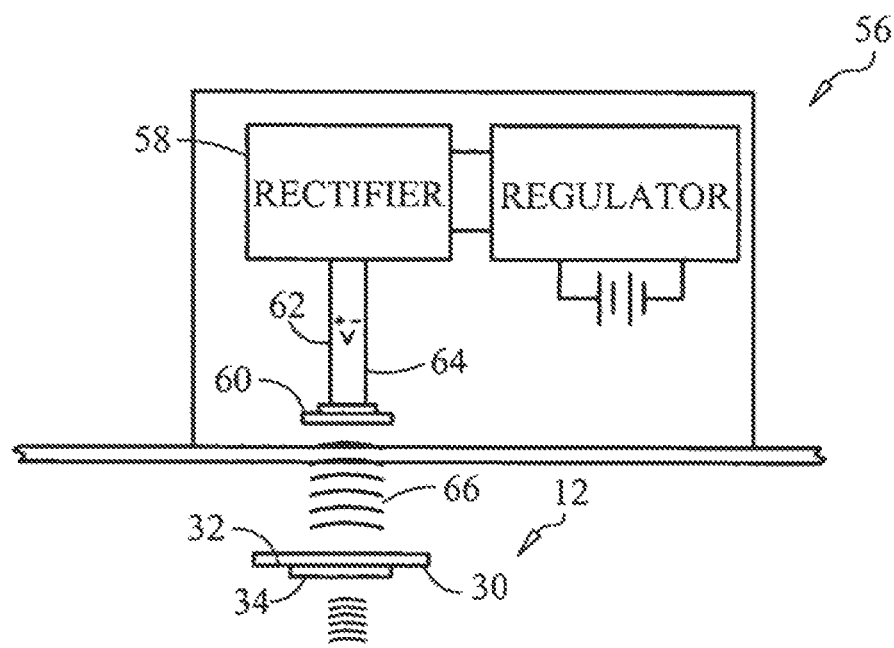
FIG. 4 depicts a schematic diagram of another embodiment of an energy system according to present disclosure utilizing acoustic wave energy.

Referring now to FIG. 4, an alternative energy system is shown which utilizes acoustic waves rather than a magnetic field to power/excite the implanted medical device 12. An external energy unit 56 includes an acoustic signal source 58 connected to an emitter 60 through conductors 62 and 64. Emitter 60 includes a piezoelectric transducer or any other acoustic source capable of emitting acoustic waves receivable by the implanted medical device 12. The frequency of the acoustic waves may be in any suitable range including, but not limited to, frequencies in the ultrasonic (frequencies generally higher than 20 KHz), sonar (generally 25-100 KHz), medical ultrasonic (generally 1-10 MHz), and microwave acoustic (frequencies generally over 50 MHz) ranges. As is well known, a lotion or gel can be used in conjunction with the external energy unit to maximize the transmission of the acoustic waves though through the skin of the patient.

As noted above, medical device 12 may include a piezoelectric device 30 having a ferromagnetic plate 32 attached to a ceramic disk 34. In operation, waves 66 from the emitter 60 impinge on piezoelectric device 30 causing plate 32 and piezoelectric ceramic disk 34 to vibrate and emit a convergent point shockwave. In a preferred embodiment, the frequency of the waves emitted by the emitter 60 may be selected to match the resonate frequency of the piezoelectric device 30 to optimize vibration.

An alternative energy system uses extracorporeal shockwaves (ESW) to power/excite the implanted medical device 12. The ESW system includes an energy source (the shockwave generator), a focusing system, and a coupling mechanism.

The shockwave generator can take the form of electrohydraulic, piezoelectric, and/or electromagnetic energy. In an electrohydraulic generator, an electrical discharge of a high-voltage current occurs across a spark-gap electrode located within a fluid-filled container. The electric discharge results in a vaporization bubble, which expands and immediately collapses, generating a high-energy pressure wave. In a piezoelectric generator hundreds-to-thousands of ceramic or piezo crystals are set in a fluid-filled container and are stimulated with a high-energy electrical pulse. The high-energy electrical pulse vibrates or rapidly expands the crystals, leading to a shockwave that can be propagated through the fluid. In an electromagnetic generator, an electrical current is applied to an electromagnetic coil mounted within a fluid-filled cylinder. The magnetic field causes an adjacent metallic membrane to be repelled by the coil, resulting in extremely rapid movement of the membrane, producing a shaped shockwave. Exemplary shockwave generators are provided in U.S. Pat. Nos. 2,559,227, 4,947,830 and 5,058,569, the contents of which are herein incorporated by reference.

The focusing system concentrates and directs the shockwave energy into the body of the patient. For example, an electrohydraulic system utilizes the principle of the ellipse to direct the energy created from the spark-gap electrode. Piezoelectric systems arrange their crystals within a hemispherical dish, arranged so that the energy produced is directed toward one focal point. Electromagnetic systems use either an acoustic lens or a cylindrical reflector to focus their waves.

The coupling system transmits the energy created by the shockwave generator to the skin surface and through body tissues into the patient. The coupling system can take the form of a large water bath in which the patient is submerged. Alternatively, the coupling system can be small pools of water or water-filled cushions with a silicone membrane to provide air-free contact with the patient's skin.

In the above embodiments, the external energy unit 10 transmits a steady energy signal to the energy focusing device 28, resulting in a steady treatment energy signal to the treatment site. It is contemplated that the external energy unit 10 may provide a pulsated energy signal to the energy focusing device 28, resulting in pulsated treatment energy delivered to the treatment site. Additionally, the frequency and/or wavelength of the transmitted energy may be modulated, thereby modulating the treatment energy signal.

It should be emphasized that the present disclosure is not limited to the energy units described above. Other energy units include, but are not limited to, radio frequency (RF), magnetic, electro magnetic (EM), acoustic, microwave, thermal, vibratory, radiation, or extracorporeal shockwave (ESW) energies, alone or in any combination thereof. Furthermore, the frequency and/or wavelength of the transmitted energy may be adjusted, depending of the depth, size, density, location, etc. of the treatment site.

Figure 5:
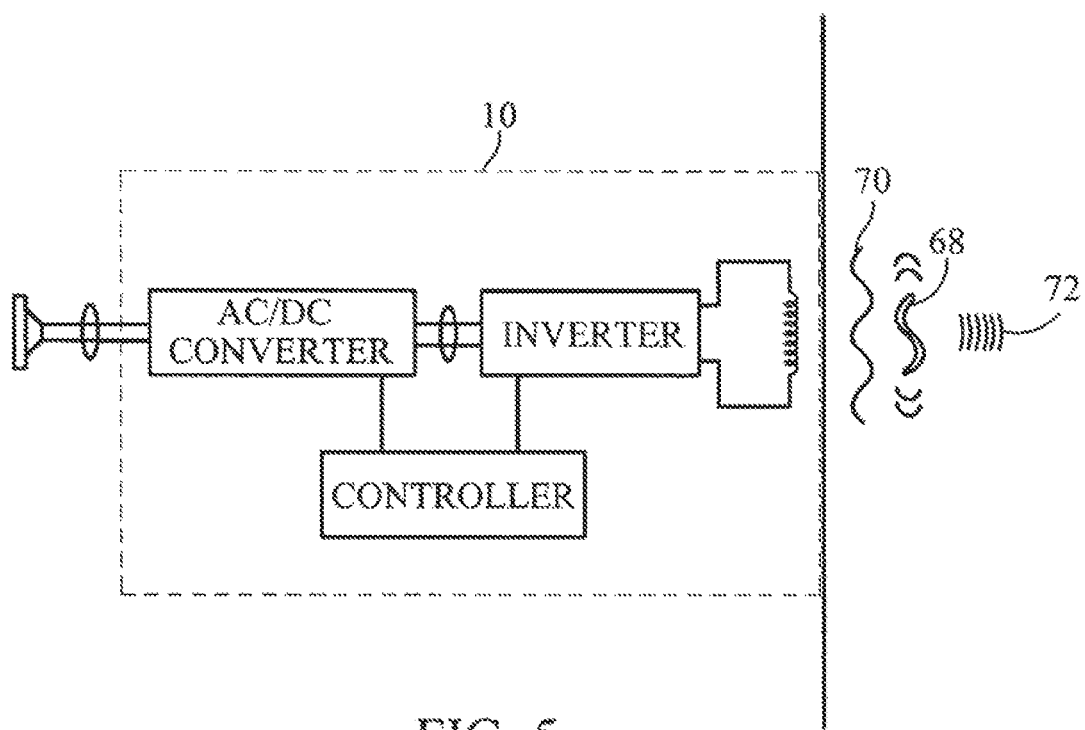
FIG. 5 depicts one embodiment of a shaped wire energy focusing device according to the present disclosure.

In the foregoing embodiments, the energy focusing device 28 has been described as including a piezoelectric device 30. However, in alternate embodiments any energy focusing device 28 may be used which can convert externally transmitted energy into an in vivo focused energy source, such as a convergent point shockwave. Referring to FIG. 5, an alternative embodiment is shown wherein energy focusing device 28 includes a shaped wire or rod 68 configured for receiving and radiating the externally transmitted energy 70. The shaped wire 68 resonates when exposed to the externally transmitted energy 70 from an external energy unit 10. The frequency of the signal 70 and the configuration of the shaped wire 68 may be selected such that shaped wire 68 resonates when exposed to the transmitted energy, emitting a convergent point shockwave. For example, the frequency of the transmitted energy and the configuration of the shaped wire 68 may be selected such that the shaped wire 68 resonates at a frequency of about between 1-10 MHz. As previously noted, the frequency or wavelength may be varied.

In the foregoing embodiments, the energy focusing device 28 has been described as any energy focusing device 28 which can convert externally transmitted energy into a convergent point shockwave. However, it is contemplated that the energy focus device 28 may be any device which is configured to receive and convert an external energy signal into an internal energy, directing the internal energy into the treatment site. Non-limiting example of the converted and directed internal energies include, radio frequency (RF), magnetic, electro magnetic (EM), acoustic, microwave, thermal, vibratory, radiation, or extracorporeal shockwave (ESW) energies, alone or in any combination thereof.

Figure 6:
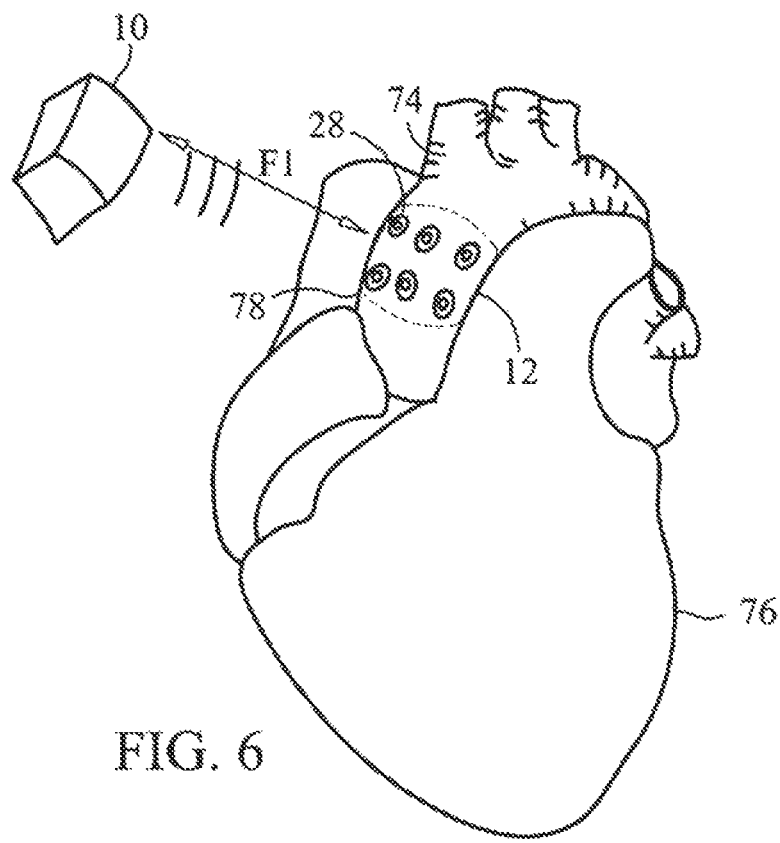
FIG. 6 depicts one embodiment of an implantable medical device of the present disclosure positioned on an outer surface of a patient's heart.
Figure 7:
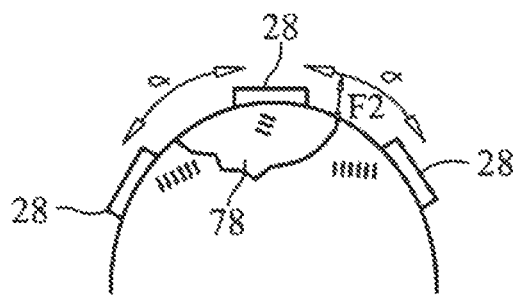
FIG. 7 depicts another embodiment of an implantable medical device of the present disclosure including multiple energy focusing devices positioned in angular relation.

Referring now to FIGS. 6 and 7, one exemplary practical application of an energy unit according to the present disclosure is shown wherein the implanted medical device 12 is implanted or surgically positioned on or proximal to an outer surface of the aorta 74 of the heart 76. Imaging techniques, such as MRI, CT scan, ultrasound, x-ray, fluoroscope, etc., may be used in the implantation of the medical device 12, aiding in the positioning of the medical device 12. Medical device 12 is implanted at a distance F1 from the skin surface of the patient. The implanted medical device 12 is positioned adjacent to a treatment site 78, which may be, for example, an area of recurring clotting or stenotic area. At periodic time intervals, the implanted medical device 12 may be activated to break-up or fragment particulate material to treat, for example, clotting or stenosis. As discussed above, the implanted medical device 12 is activated by positioning the external energy unit 10 on the skin of the patient's body, adjacent to and aligned with the implanted medical device 12. Energy is transmitted through the body of the patient to the implanted medical device 12, such that the energy signal is transmitted to the energy focusing device. The implanted medical device 12 is positioned on the treatment site 78 such that the energy focusing device 28 directs the energy signal into the treatment site 78. For example, the energy focusing device 28 creates a convergent point shockwave focused into the clot or stenotic area at a distance F2 from the energy focusing device 28, breaking-up or fragmenting particulate material in the clot or stenotic area. The energy focusing device 28 can be used for a single treatment or multiple treatments.

In one alternative embodiment, the implanted medical device 12 includes a plurality of energy focusing devices 28, implanted or surgically positioned on or proximal to an outer surface of the aorta 74 of the heart 76 of the patient. Each of the energy focusing devices 28 is positioned adjacent to a treatment site 78, an area of recurring clotting or stenotic areas. Each of the energy focusing devices 28 may be activated by positioning an external energy unit 10 on the skin of the patient's body, adjacent to and aligned with each of the energy focusing devices 28. In this regard, energy may be transmitted through the body of the patient to each of the energy focusing devices 28. Each of the energy focusing devices 28 may be activated by a single type of energy unit 10 or different energy focusing devices 28 may be activated by different types of energy units 10. For example, a first energy focusing device may be activated by ultrasonic energy and a second energy focusing device may be activated by a RF signal. Similarly, the energy focusing devices 28 may be configured to receive and/or transmit a single frequency/wavelength or a range of frequencies/wavelengths.

It may be beneficial to have a first group of energy focusing devices 28 that is responsive to a first range of frequencies and a second group of energy focusing devices 28 that is responsive to a second range of frequencies, with the first range differing from the second range. For example, if the first group is located in a different area of medical device 12 than the second group, treatment area 78 can be localized. It may also be advantageous to have the first and second groups intermingled. In this situation, activation of only one of the groups would provide a given level of energy that may be sufficient for the desired effect. If it is not, activation of the second group can be initiated (while maintaining activation of the first group) to increase the level of energy. Thus, the intended clinical result can be achieved, while minimizing potential deleterious effects, such as tissue necrosis, of unneeded energy levels.

The plurality of energy focusing devices 28 may be positioned about a single treatment site 78, wherein the energy focusing devices 28 may be activated in unison or selectively to broadly cover the treatment site 78. In one embodiment, the energy focusing devices 28 may be positioned at angular relationships .alpha. to each other, directing the convergent shockwaves into the treatment site at differing angles, such that the angles of the convergent shockwaves intersect at specific angles or depths within the treatment site to fragment particulate material. In an alternative embodiment, each of the energy focusing devices 28 may be activated individually, wherein each energy focusing device 28 may be attuned to a different activation frequency to selectively activate vibration points or convergent point shockwaves, as may be desired by a physician practitioner.

In another alternative embodiment, each of the plurality of the energy focusing devices 28 may be positioned at different treatment sites. In operation, an individual energy focusing device 28 may be selected for activation dependent on the presence of clotting or a stenotic area. The selected energy focusing device 28 may be activated by positioning an external energy unit 10 on the skin of the patient's body, aligned with the selected energy focusing device 28. Energy is transmitted through the body of the patient to the selected energy focusing device 28. The selected energy focusing device 28 is positioned on the treatment site such that a shockwave is directed into the treatment site 78, fragmenting or breaking-up the clot or stenotic area. In one embodiment, each of the energy focusing devices 28 is attuned to activate at substantially the same frequency. Alternatively, each of the energy focusing devices 28 may be attuned to be activated at different frequencies. Although the foregoing exemplary embodiment has been described using a single type of external energy unit for activating the energy focusing devices 28, it is contemplated that multiple types of external energy units may be used, wherein individual implanted medical devices may be activated by different energy units.

In the above examples, the present disclosure has been described as treating clotting and stenotic areas in the heart. However, it is contemplated that the present disclosure can be used on any organ or portion of the body requiring periodic breaking or fragmenting of particulate material, burning off endothelium or tissue overgrowth, breaking up or preventing scar tissue after surgery, breaking-up adhesions or damage to the intestines or other areas, treating tumors or carcinogenic tissue, breaking up calcific deposits, including myossitis ossificans or heterotopic tissue. For example, the present disclosure can be used on the kidney to aid in the breaking-up or fragmenting of kidney stones. Alternatively, the present disclosure can be used at joints in the body to break-up calcium deposits.

In addition to or in combination with breaking-up particulate material, the present disclosure can be used in the treatment of vessel spasm. For example, during any acute myocardial infarction the blood flow is reduced due to a clotting of the vessel. Additionally, the vessel can vasospasm, narrowing vessel diameter and thereby further reducing the flow of blood. The present disclosure can treat the vasospasm by directing energy into the vessel, dilating the vessel to increase the blood flow therein. Furthermore, during a procedure to remove the clotting material an energy focusing device 28 of the present disclosure can be positioned adjacent to the vessel to focus energy into the vessel. The energy is focused on the vessel to relieve the vasospasm, increasing the diameter of the vessel. The increased diameter of the vessel has the beneficial effect of recreating a laminar flow in the once restricted portion of the vessel. It is contemplated that the present disclosure can be used singularly or in combination with vasospasm treating medication. The above example noted the treatment of vasospasms, however the present disclosure can be used to treat any spasm in a vessel, for example reflux, colorectal spasm, etc.

In another exemplary application, the present disclosure can be used in fertility treatment (or conversely, birth control). Energy can be applied to stimulate release of an egg from the ovaries and into the fallopian tubes. As noted above, energy can be applied to control the travel of the egg through the fallopian tubes. The energy can also be used to increase motility of the sperm.

Applicant's published U.S. patent applications, U.S. Publication Nos. 2004/0084568 and 2004/0084569, the contents of which are herein incorporated by reference, are relevant in this regard. In these applications, the use of energy to modulate drag and thrust is disclosed. The drag is actively modulated by energy beams which may either increase or decrease the drag. The energy beams may provide energy at a transition region between turbulent and laminar flows or at the leading edge of a laminar flow in order to facilitate the respective increase or decrease in drag. These principles are readily transferable to flow within vessels of the body.

The present disclosure has been previously described as treating or breaking particulate material in the body of the patient. However, it is contemplated that the present disclosure can be used to elicit localized biological responses in the body of the patient. For example, the breaking-up or fragmentation can result in a localized release of enzymes, proteins, or viral RNA from within the cells or externally. The use of commercially available factors such as OP-1 (from Stryker Corporation) and INFUSE (from Medtronic) is also contemplated. Additionally, the present disclosure can be used to accelerate or reduce the lysis, especially when used in combination with pharmaceutical treatments.

It is contemplated that imaging techniques and devices may be used in conjunction with the system of the present disclosure. An imaging device may be used to diagnosis the condition requiring treatment, determining the characteristic of the treatment site. Upon the application of the treatment energy from the energy focusing device 28, the imaging device may be used to determine if further treatment is required and to periodically monitor the treatment site. Acceptable imaging devices can include, but are not limited to, MRI, CT scan, ultrasound, x-ray, fluoroscope, etc. Furthermore, when used with imaging devices, such as an MRI, the energy focusing device 28 may act as a secondary coil, providing greater clarity of the treatment site.

Figure 8:
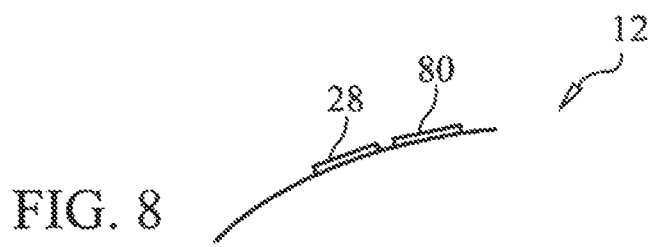
FIG. 8 depicts another embodiment of an implantable medical device of the present disclosure including a sensor assembly.
Figure 9:
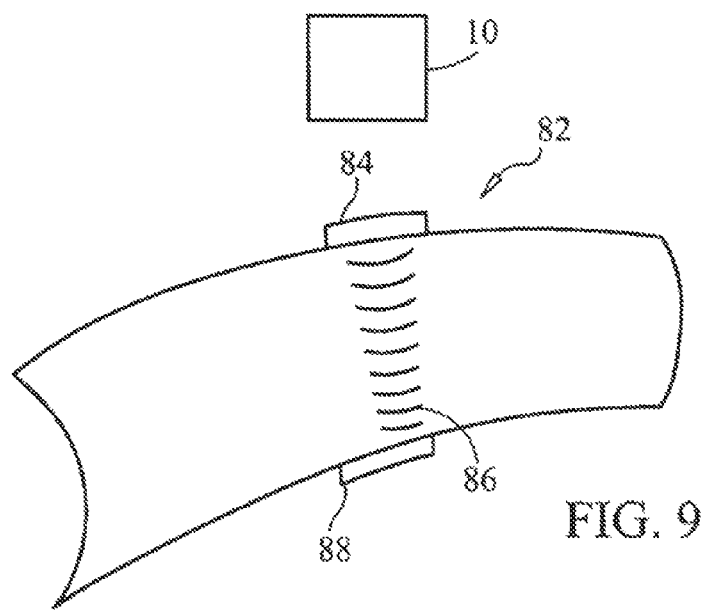
FIG. 9 depicts another embodiment according to the present disclosure including a flow sensor assembly.

Referring to FIGS. 8 and 9, in an alternate embodiment, the implanted medical device 12 may further include at least one sensor assembly 80 for monitoring the patient. An exemplary sensor assembly 80 is a flow sensor assembly 82 for monitoring the blood flow through an artery, vein, or other vessel. The flow sensor assembly 82 includes a transducer 84 for transmitting an acoustic signal 86 and a receiver 88 for receiving the acoustic signal 86. The flow sensor assembly 82 is used to monitor the flow of blood, including the velocity and volume through the vessel. The flow sensor assembly 82 can be activated by a signal from the external energy unit 10 or can be programmed to transmit readings at given intervals or when a recorded parameter exceeds a given threshold level. Exemplary flow sensor assemblies 82 are disclosed in U.S. Pat. No. 6,398,743, to Cimochowski et al., the content of which is incorporated by reference. Other sensor assemblies that may be used with the present disclosure can include, but are not limited to, temperature sensor assemblies, pressure sensor assemblies, tension sensor assemblies, and density sensor assemblies, etc.

As is well-known, the sensor assemblies can include means for transmitted the measured parameters to a remote location so that a trained healthcare provider can monitor the readings. Pending U.S. patent application Ser. No. 10/421, 965 filed Apr. 23, 2003, the contents of which are incorporated by reference, discloses one mechanism that can be used in this regard.

In alternate embodiments, sensor assemblies may be used in conjunction with any type of implantable medical device such as, but not limited to, tissue grafts, screws, plates, rods, prosthetic devices, etc. The sensors could be made to include any suitable material, including but not limited to, wires, capacitors, silicone chips, and partial or completely biodegradable materials. The sensors could also be made to detect heat variations, cooling energy, pH gradients, electrical charge, electrolytes, magnetic charge, changes in local chemistry, etc., and may be designed to monitor such things as loosening of implants, the stability of hardware, or the growth rate of cancer, among other things. The sensor can be made of or partial made of a biodegradable or bioreabsorble material, which can include, but not be limited to, silicone, iron, or copper.

Referring now to one embodiment of a method of use of the present disclosure, medical device 12 is surgically positioned on a vessel and located at an area of reoccurring plaque build-up, for example. The implantable medical device 12 generally includes a plurality of energy focusing devices 28 and at least one flow sensor assembly 82. The energy focusing devices 28 and the flow sensor assembly 82 are preferably attuned to be activated at different frequencies transmitted from an external energy unit 10. Initially, the baseline blood flow through the vessel in a clean state, absent plaque, is determined. The baseline blood flow may be determined using the flow sensor assembly 82 or other known devices. At a set time interval, or check-up date, the vessel may be subsequently checked for plaque build-up or stenosis. To check the vessel, the flow sensor assembly 82 may be activated by positioning the external energy unit 10 on the skin of the patient's body, adjacent to and aligned with the flow sensor assembly 82. Energy is transmitted through the body of the patient to the flow sensor assembly 82. The external energy unit 10 transmits the energy at a first frequency, attuned to activate the flow sensor assembly 82. The flow sensor assembly 82 is positioned on the vessel such that an acoustic signal is directed into the vessel to determine the blood flow in the vessel. If the blood flow is less then the baseline blood flow, plaque may be present in the vessel.

To break-up or fragment the plaque, one or more of the energy focusing devices 28 are activated. As discussed above, each of the energy focusing devices 28 may be activated by positioning the external energy unit 10 on the skin of the patient's body, aligned with the energy focusing device 28. In a preferred embodiment, energy is transmitted through the body of the patient to the energy focusing device 28 at a second frequency attuned to activate one or more of the energy focusing devices 28. The energy focusing devices 28 are positioned on the vessel such that a convergent point shockwave may be directed from each energy focusing device 28, breaking-up the plaque or fragmenting particulate material that may be causing restricted blood flow.

The blood flow through the vessel may then be rechecked using the flow sensor assembly 82, and compared to the baseline blood flow. If the blood flow is substantially equal to the baseline blood flow the treatment is ended. If the blood flow is less then the baseline blood flow, the treatment may be repeated, as desired by a physician practitioner. This process may be continued until the blood flow is substantially equal to the baseline blood flow or a suitable amount of flow is achieved, as determined by a physician practitioner.

In alternate embodiments, the implanted medical device 12 can include a plurality of sensor assemblies 80 and energy focusing devices 28 positioned along and about the vessel. The sensor assemblies 80 may be used in conjunction to determine the position of the plaque build-up in the vessel, and to select which of the energy focusing device(s) 28 is to be activated or used to break-up the plaque or fragment the particulate material.

Figure 10:
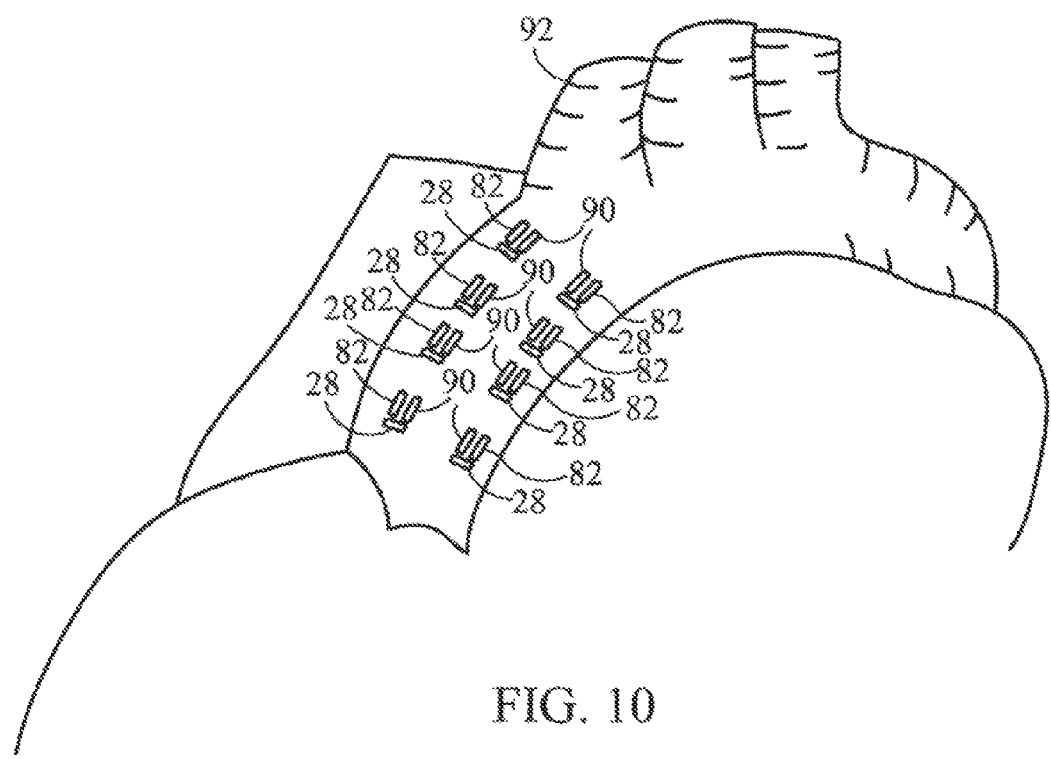
FIG. 10 depicts another embodiment of an implantable medical device of the present disclosure including a plurality of sensor assemblies.

Referring to FIG. 10, in one embodiment the implanted medical device 12 includes a plurality of flow sensor assemblies 82 and density sensor assemblies 90, positioned along and about the vessel. Adjacent to each pair of sensor assemblies 82 and 90 is an energy focusing device 28. Each of the sensor assemblies 82 and 90 and the energy focusing devices 28 may be attuned to different activation frequencies. For example, the density sensor 90 can be an ultrasonic sensor and may also be used to determine the depth of the plaque.

In operation, the sensor assemblies 82 and 90 may be initially activated by positioning the external energy unit 10 on the skin of the patient's body, aligned with the vessel 92. Energy is transmitted through the body of the patient to the sensor assemblies 82 and 90. The frequency/wavelength of the energy may be selectively modulated, or in the alternative, continually modulated to individually activate the sensor assemblies 82 and 90. In this regard, the flow sensor assemblies 82 may determine the blood flow at different locations along the vessel 92. The density sensor assemblies 90 may determine the vessel wall thickness, including plaque thickness, at different locations. The information from the individual sensor assemblies 82 and 90 may be used to construct an image of the vessel 92 for viewing on an external monitor, wherein the physician practitioner may use the information to determine and adjust the treatment. Using the constructed image, the appropriate energy focusing device(s) 28 may be selected for activation to break-up or fragment the plaque or particulate material. After an initial treatment with the energy focusing device(s) 28, the vessel can be re-imaged to determine if further treatment is required. This process may be repeated until the vessel 92 is substantially free of plaque build-up or a suitable amount of flow is achieved, as determined by a physician practitioner.

In one alternative embodiment, the medical device 12 of the present disclosure is positioned proximal to a joint in the body of a patient. The medical device includes pressure sensor assemblies positioned proximal to or within the joint. Energy focusing devices 28 are positioned to direct a convergent point shockwave into the joint. The pressure sensor assemblies may be used to detect an increase joint pressure, which may indicate a buildup of particulate material within the joint. As described above, the energy focusing devices 28 may then be activated, directing a convergent point shockwave into the joint, to break-up or fragment the particulate material, relieving the pressure in the joint.

Figure 11:
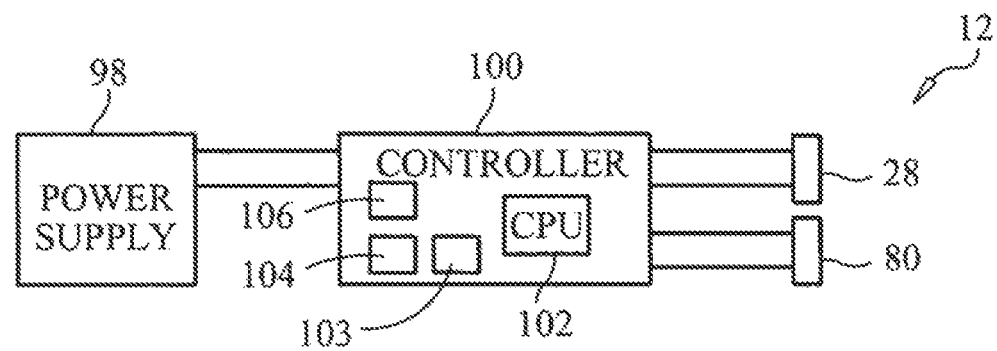
FIG. 11 depicts another embodiment of an implantable medical device of the present disclosure including a power supply.

Referring to FIG. 11, in one alternate embodiment the implanted medical device 12 may further include a power supply 98 operably connected to the energy focusing device (s) 28 and the sensor assembly(s) 80. A control unit 100 including a processing unit 102 is interposed between the energy focusing device(s) 28 and the sensor assembly(s) 80 and the power supply 98. In operation, the control unit 100 is configured to selectively activate the sensor assembly(s) 80 to image the vessel at a set time interval. In response to the imaging, if required, the control unit 100 may also selectively activate one or more energy focusing device(s) 28 to break-up the plaque or fragment particulate material that may be causing restricted blood flow. After an initial treatment with the energy focusing device(s) 28, the vessel may be re-imaged to determine if further treatment is required. This process may repeated until the vessel is substantially free of plaque or a suitable amount of flow is achieved, as may be determined by pre-set parameters programmed into control unit 100.

In an embodiment, the control unit 100 may be controlled from an external unit. The control unit 100 further includes a transceiver 103 configured to receive an external signal. The transceiver 103 activates or deactivates the medical device 12 in response to the external signal. For example, the transceiver may be configured to receive an RF signal.

In another alternate embodiment, the control unit 100 may further include electronic memory 104, for storing imaging and treatment information. A transmitter 106 may be included for downloading the stored information to an external receiving unit. The external receiving unit can be a computer, including a CPU and a display unit, or any other processor. The computer can be connected to a global computer network, allowing the stored information to be transmitted across the global computer network to remote medical personnel. The stored information can provide a continual history of the patient's plaque build-up and subsequent treatment(s) for review and analysis by medical practitioners. The electronic memory 104 may include a radio frequency identification chip (RFID), which is activated by an RF signal to transmit the stored information.

Figure 12:
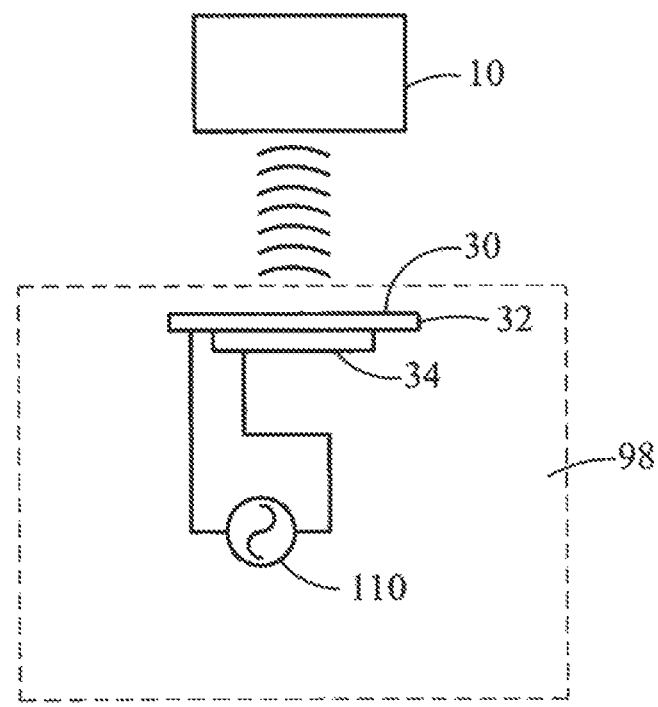
FIG. 12 depicts the device of FIG. 11 including a rechargeable power supply.

Referring to FIG. 12, in one embodiment the power supply 98 includes a rechargeable battery 110. The rechargeable battery 110 may be recharged by positioning the external energy unit 10 on the skin of the patient's body, adjacent to and aligned with the rechargeable battery 110. Energy is transmitted through the body of the patient to the rechargeable battery 110. In one embodiment, the rechargeable battery 110 includes a piezoelectric device 30. As noted above, an exemplary piezoelectric device 30 includes a ferromagnetic plate 32 attached to a ceramic disk 34. The external energy unit 10 causes the piezoelectric ceramic disk 34 to vibrate generating a voltage which recharges battery 110. An exemplary energy system for non-invasively recharging an implant rechargeable battery is disclosed in U.S. Pat. No. 5,749,900, to Schroeppel, the contents of which are incorporated by reference. Alternatively, the external energy system may be percutaneously or transcutaneously positioned proximal to the rechargeable battery 110.

In the above embodiment, the rechargeable battery 110 is described as requiring an external energy unit 10 to be recharged. However it is contemplated, that the rechargeable battery can include a self-recharging mechanism. The self-recharging mechanism utilizes the movement of the patient to generate power to recharge the rechargeable battery.

Figure 13A:
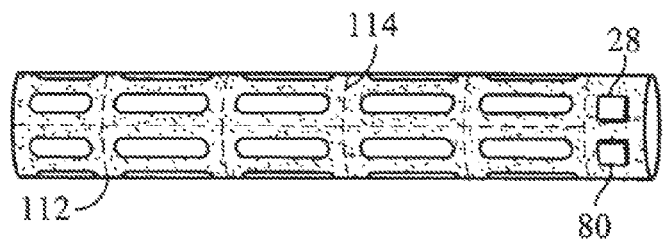
FIGS. 13A-B depicts another embodiment of an implantable medical device of the present disclosure including a stent.
Figure 13B:
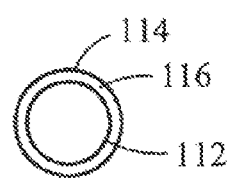

Referring to FIG. 13A-B, in one alternative embodiment, the implanted medical device 12 may include a stent 112, positionable in a vessel of a patient. The stent 112 includes at least one energy focusing device 28. As noted above, an exemplary energy focusing device 28 is a piezoelectric device 30 which includes a ferromagnetic plate 32 attached to a ceramic disk 34. The piezoelectric device(s) 30 can be activated by positioning an external energy unit 10 on the skin of the patient's body, aligned with the piezoelectric device(s) 30. Energy is transmitted through the body of the patient to the piezoelectric device(s) 30. The piezoelectric device(s) 30 is positioned on the stent 112 to prevent restenosis or plaque build-up.

In an alternative embodiment, a plurality of energy focusing devices 28 may be positioned on and about stent 112. Each of the energy focusing devices 28 may be activated by positioning an external energy unit 10 on the skin of the patient's body, aligned with the energy focusing devices 28. Energy is transmitted through the body of the patient to the energy focusing devices 28 (or a given subset as previously described). The implanted stent 112 may further include at least one sensor assembly 80 positioned on the stent 112 for monitoring various conditions of the patient. As noted above, an exemplary sensor assembly 80 is a flow sensor 82 for monitoring the blood flow through the vessel. The flow sensor assembly 80 may be used to monitor the flow of blood, including the velocity and volume through the stent. If flow sensor assembly 80 detects a decrease in the blood flow through the stent 112, restenosis or plaque build-up may be present. The energy focusing device 28 can then be activated to break-up or fragment the particulate material. An exemplary stent 112 including a sensor assembly is disclosed in U.S. Pat. No. 5,967,986, to Cimochowski et al., the contents of which are incorporated by reference.

In the above exemplary embodiments, the present disclosure is utilized to break-up or fragment particulate material within the body of the patient. In an alternative embodiment, the present disclosure can be used to elicit a localized biological response in the body of the patient. The present disclosure can provide a disruptive energy causing a localized change in temperature, change in PH, or local cellular damage. This can result in the release of enzymes, proteins, or viral RNA (or the previously identified commercially available products) from within the cells or externally. Additionally, an increase in temperature can have the beneficial effects aiding in the alleviation of localized pain, fighting of local infections, and increasing vascular flow and permeability of vessels at the treatment site.

While in the foregoing exemplary embodiment the implanted medical device 12 was depicted specifically with a stent 112, the energy focusing device 28 and sensor assemblies 80 may be used in conjunction with other types of implantable medical devices 12. Non-limiting examples include hip and knee replacements (total and partial), spinal implants, tissue scaffolds, tissue fasteners, screws, plates, rods, prosthetic devices. Furthermore, the implantable medical devices 12 may be a biodegradable, bioreabsorbable, and/or biologic implant, including tissue scaffolds which may include stem or fetal cells, tissue grafts, cellular implants, organ transplant implants, biologic grafts, osteochondral grafts, autografts, allografts, or xenografts.

Applicant's published U.S. patent application, U.S. Publication No. 20040078073, the contents of which are incorporated by reference, discloses tissue scaffolds and associated methods. The present disclosure can be used to improve the fragmentation of these scaffolds so they would become more biologically tolerated. In other words, the stem cells or fetal cells in the scaffold would remain viable, but the scaffold could be degraded as needed. Once the tissue starts to function, the tissue scaffold could be externally broken up and ensure their more rapid degradation while the cells or cell therapy remain viable within the body. In order to hasten the degradation, energy could be applied to accelerate the degradation of the scaffold without affecting the cell viability. Voids or defects could be placed into the scaffold, such as bubbled areas. These would serve as preferential areas of degradation. As has been previously discussed, the energy applied could be selected to lyse the cells, thereby releasing enzymes, hormones, etc. This would effective create a localized biological or gene therapy.

Figure 14:
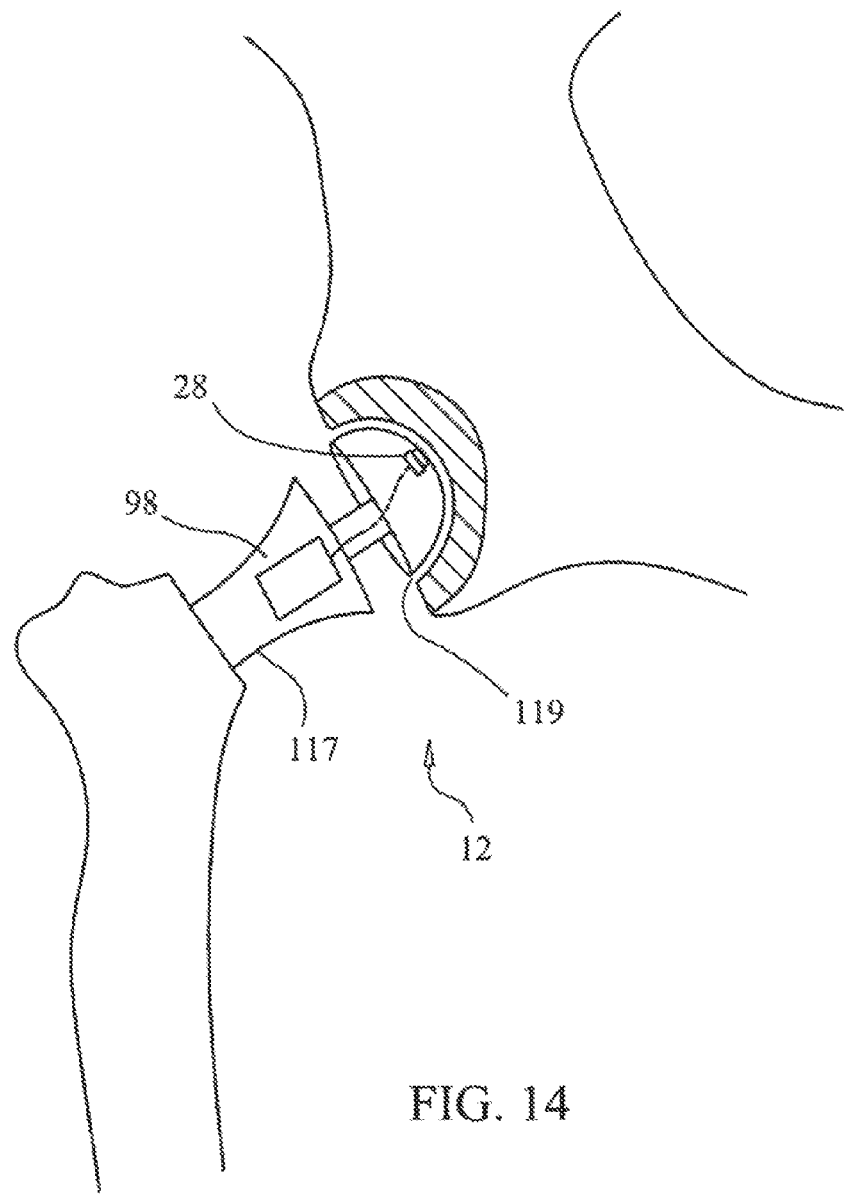
FIG. 14 depicts another embodiment of an implantable medical device of the present disclosure including a hip replacement.

Referring to FIG. 14, the implantable medical device 12 includes a hip replacement system 117. The energy focusing device is positioned on or incorporated into the hip replacement 117 to transmit energy into the hip joint 119. Additionally, the internal power supply 98 may be attached to or incorporated into the hip replacement 117.

Referring again to FIGS. 13A-B, the exemplary stent 112 may be coated with a pharmaceutical agent 114. The pharmaceutical agent 14 may be physically and/or chemically bonded to the surface of the stent 114 by, for example, but not limited to, covalent bonding, ionic bonding, VanderWal forces, magnetic forces, etc. For example, numerous pharmaceutical agents are being actively studied as antiproliferative agents to prevent restenosis and have shown some activity in experimental animal models. These include, but are not limited to, heparin and heparin fragments, colchicine, taxol, angiotensin converting enzyme (ACE) inhibitors, angiopeptin, Cyclosporin A, goat-anti-rabbit PDGF antibody, terbinafine, trapidil, interferon-gamma, steroids, ionizing radiation, fusion toxins, antisense oligonucleotides, gene vectors, and rapamycin. An exemplary stent 112 including a pharmaceutical agent 114 coated thereon is disclosed in U.S. Pat. No. 6,585,764, to Wright et al., the contents of which are incorporated by reference. Applicant's U.S. Pat. No. 5,163,960, the contents of which are incorporated herein by reference, discloses an implant device (including an expandable device) may be provided with a coating that contains a therapeutic agent.

In addition to or as an alternative to, the stent 112 may be coated with a therapeutic or biologic agent. Non-limiting examples include hormones, cells, stem cells, bone morphogenic proteins (BMPs), enzymes, proteins, RNA, etc.

Figure 15:
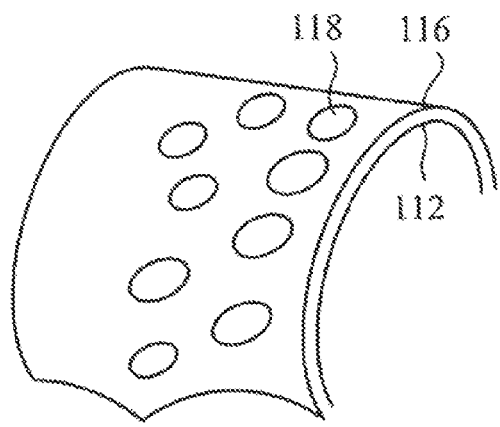
FIG. 15 depicts the stent of FIGS. 13A-B including a porous coating.

In one embodiment of the present disclosure, a pharmaceutical agent 114 may be affixed to the stent 112 by coating, mixing, or bonding the pharmaceutical agent 114 to a polymer coating 116 applied to the stent 112. In this regard, the polymer coating 116 may be configured to be a reactive coating, reacting to energy provided by an external energy unit 10. Referring to FIG. 15, in one exemplary embodiment, the polymer coating 116 is a porous coating, which acts as a membrane to diffuse the pharmaceutical agent 114. Initially, the pores 118 in the coating are closed or sufficiently small in size to restrict the release of the pharmaceutical agent 114. In operation, the external energy unit 10 may be positioned over the stent 112 and provide energy to heat the stent 112 and polymer coating 116, opening or increasing the size of the pores 118 to selectively release the pharmaceutical agent 114. After a therapeutic amount of the pharmaceutical agent 114 has been released, the applied energy may be discontinued, closing the pores 118. The polymer coating 116 may be attuned for activation at substantially the same frequency as the energy focusing device 28. Alternatively, polymer coating 116 may be attuned to be activated at a different frequency from that of the energy focusing device 28.

Figure 16:
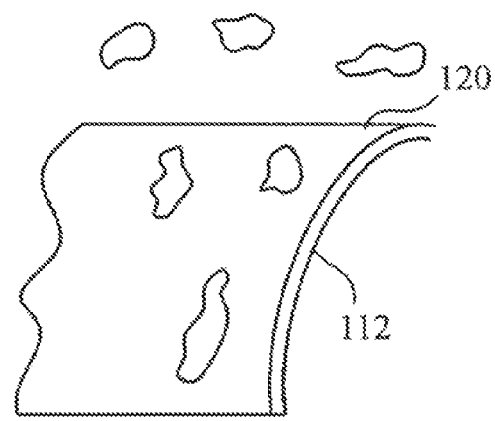
FIG. 16 depicts the stent of FIGS. 13A-B including a biodegradable coating.

Referring to FIG. 16, in another embodiment, the polymer coating 116 may be a biodegradable coating 120. In operation, the external energy unit 10 may be positioned over the stent 112, providing energy at a frequency to heat the stent 112 and polymer coating 116, partially breaking-up or fragmenting the biodegradable coating 120 from the stent 112. The applied energy increases the degradation, fragmentation, or dissolution rate of the biodegradable coating 120, to accelerate the release of the pharmaceutical agent 114. After a therapeutic amount of the pharmaceutical agent 114 has been released, the energy may be discontinued. The biodegradable coating 120 may be attuned for activation at substantially the same frequency as the energy focusing device 28. Alternatively, biodegradable coating 120 may be attuned to be activated at different frequency from that of the energy focusing device 28.

In an embodiment, stent 112 may include a plurality of layers or sections of biodegradable coatings 120, each including a different therapeutic amount of a pharmaceutical agent 114. The external energy unit 10 may be used to apply energy to selectively release a layer of the biodegradable coating 120, releasing the corresponding therapeutic amount of a pharmaceutical agent 114. Each of the layers or sections of the biodegradable coating 120 may be released as needed or at set time intervals.

Similarly, the plurality of layers or sections of biodegradable coatings 120 may each including a different pharmaceutical agent 114. The external energy unit 10 may be used to apply energy to selectively release a layer of the biodegradable coating 120, releasing the corresponding pharmaceutical agent 114. Each of the layers or sections of the biodegradable coating 120 may be released as needed or at set time intervals.

Non-limiting examples of the biodegradable coating 120 include polyactic acid ("PLA"), polyglycolic acid ("PGA"), and copolymers thereof. The degradation rate of the biodegradable coating can be controlled by the ratio of PLA to PGA, or by the thickness or density of the coating. Additionally, the biodegradable coating 120 may also include collagen, cellulose, fibrin, or other cellular based compounds.

In an alternate embodiment, the polymer coating includes micro capsules, spheres, or crystals affixed to and around the stent 112. The pharmaceutical agent 114 is contained within the micro capsule, spheres, or crystals. In operation, the external energy unit 10 may be positioned over the stent 112, providing energy at a frequency to heat the stent 112 and polymer coating 116, breaking off a number of the micro capsules from the stent 112. The applied energy increases the degradation, fragmentation, or dissolution rate of the micro capsules to accelerate the release of the pharmaceutical agent 114. After a therapeutic amount of the pharmaceutical agent 114 has been released, the energy may be discontinued.

While the foregoing exemplary embodiment was depicted specifically with a stent 112, in alternate embodiments, similar techniques may be used to coat other types of implantable medical devices, such as hip and knee replacement (total and partial), spinal implants, scaffold, biological implants or grafts, tissue grafts, screws, plates, rods, prosthetic devices, etc. A wide array of types of drugs may be delivered in a similar fashion as described above. For example, steroidal, nonsteroidals, pain relieving drugs, hormones, cells, stem cells, bone morphogenic proteins (BMPs), enzymes, proteins, RNA, and other agents may be delivered intraoperatively or postoperatively. In this regard, the coated implant may advantageously be used as a multimodal treatment regimen with postoperative analgesic pain relief and accelerate tissue healing. This may be particularly advantageous for cementless implantation, disc replacement, tissue grafts, cellular therapy, gene therapy, implanted organs such as kidney transplants or partial implants, among other applications.

In an embodiment, the implantable medical device 12 may be at least partial made of a biodegradable material. Non-limiting examples of the biodegradable materials include polyactic acid ("PLA"), polyglycolic acid ("PGA"), and copolymers thereof. The degradation rate of the biodegradable materials can be controlled by the ratio of PLA to PGA. Additionally, the biodegradable material may also include collagen, cellulose, fibrin, or other cellular based compounds.

As described above, a pharmaceutical agent 114 may be affixed to the biodegradable implant by coating, mixing, or bonding the pharmaceutical agent 114 to a polymer coating 116 applied to the biodegradable implant. In this regard, the polymer coating 116 may be configured to be a reactive coating, reacting to energy provided by an external energy unit 10.

In another alternate embodiment, the biodegradable implant may be impregnated with the pharmaceutical agent 114. In operation, the external energy unit 10 may be positioned over the biodegradable implant, providing energy at a frequency to heat the biodegradable implant, partially breaking-up or fragmenting a portion of the biodegradable implant. The applied energy increases the degradation, fragmentation, or dissolution rate of the biodegradable implant, to accelerate the release of the pharmaceutical agent 114. After a therapeutic amount of the pharmaceutical agent 114 has been released, the energy may be discontinued. The biodegradable implant may be attuned for activation at substantially the same frequency as the energy focusing device 28. Alternatively, biodegradable implant may be attuned to be activated at different frequency from that of the energy focusing device 28.

In an alternate embodiment, biodegradable implant may include a plurality of layers or sections, each including a different therapeutic amount of a pharmaceutical agent 114. The external energy unit 10 may be used to apply energy to selectively release a layer of the biodegradable implant, releasing the corresponding therapeutic amount of a pharmaceutical agent 114. Each of the layers or sections of the biodegradable implant may be released as needed or at a set time intervals.

In an alternate embodiment, the biodegradable implant is made up of micro capsules, spheres, or crystals. The pharmaceutical agent 114 is contained within the micro capsule, spheres, or crystals. In operation, the external energy unit 10 may be positioned over the biodegradable implant, providing energy at a frequency to heat the biodegradable implant, breaking off a number of the micro capsules. The applied energy increases the degradation, fragmentation, or dissolution rate of the micro capsules to accelerate the release of the pharmaceutical agent 114. After a therapeutic amount of the pharmaceutical agent 114 has been released, the energy may be discontinued.

Figure 17:
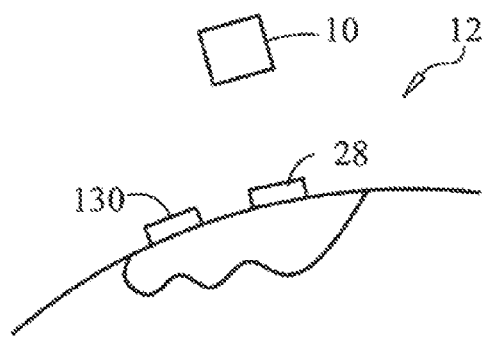
FIG. 17 depicts another embodiment of an implantable medical device of the present disclosure including a heat sink.

Referring to FIG. 17, in another embodiment, the implanted medical device 12 may include a heat sink 130, wherein the heat sink 130 may be incorporated into the medical device 12 or be positioned separate from the medical implant 12. The heat sink 130 is configured to absorb energy from the external energy unit 10, converting the energy into heat energy. The heat sink 130 stores and releases the heat energy to the treatment site over time, creating a localized increase in temperature. In one embodiment, the heat is stored in the heat sink 130 until the temperature in the surrounding tissue decreases to a threshold temperature. At this point, heat is released from the heat sink 130.

The beneficial effects of the localized increase in temperature include (but are not limited to): aiding in the alleviation of localized pain, fighting of local infections, and increasing vascular flow and permeability of vessels at the treatment site. For example, the heat sink 130 may be positioned during a surgical procedure to aid in the healing of the surgical site. The heat sink may provide a local increase in temperature at the surgical site, aiding the healing and increasing the vascularity at the surgical site to control delivery of medicaments to the surgical site.

When used in conjunction with the energy focusing device 28, the prolonged heat energy released by the heat sink 130 can soften up plaque or particulate material at the treatment site. This can assist in the fragmentation of particulate material or aid in the breaking-up of the plaque. Additionally, the heat sink 130 can be used for concentrating a pharmaceutical or therapeutic agent delivery in a localized area.

In another embodiment, the implanted medical device 12 may include a pH sink, wherein the pH sink may be incorporated into the medical device 12 or be positioned separate from the medical implant 12. The pH sink 130 is configured to absorb energy from the external energy unit 10, releasing a chemical to either increase or decreasing the local pH. For example, the pH sink includes a basic material which is released upon the application of the energy.

One potential use of this embodiment is the prevention and treatment of osteoporosis. Calcium from bones is used to counteract acidic conditions, leading to bone stock with decreased mineral content. This uptake of calcium can be reduced with a pH sink that releases a basic substance in the presence of an acidic environment.

Figure 18:
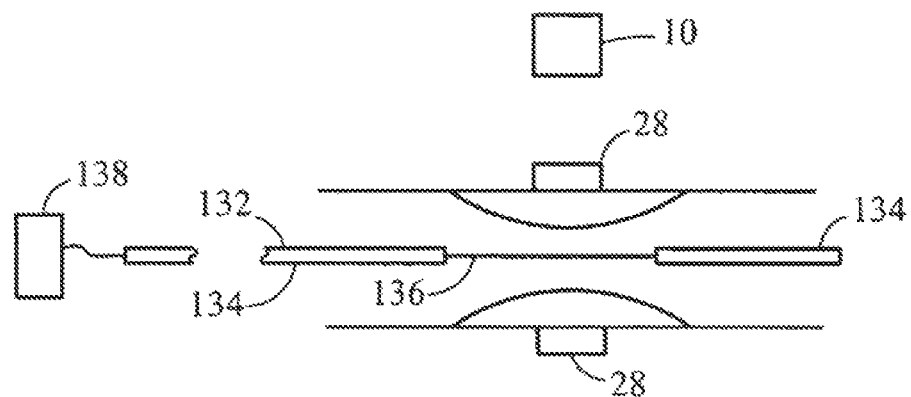
FIG. 18 depicts another embodiment of an implantable medical device of the present disclosure including a partial coated wire assembly.

Referring to FIG. 18, one embodiment of the present disclosure may further include a partially coated wire 132, for insertion into a vein, artery, or other vessel. The partially coated wire 132 includes an insulated coating 134, having an exposed portion 136 at its distal end. In operation, the exposed portion 136 may be positioned in the treatment site, adjacent to the plaque or particulate material to be fragmented. The partially coated wire 132 can be percutaneously or transcutaneously inserted into the vessel, wherein the partially coated wire 132 is moved through body of the patient to the treatment site. An external power source 138 is connected to the wire, such that energy may be provided to the treatment site from the exposed portion 136. The insulted coating 134 prevents the release the energy along the length of the coated wire, protecting the adjacent tissue. The released energy can take the form of acoustic or heat energy, aiding in the fragmentation of particulate material or removal of plaque.

Rather then being a wire with a solid core, a catheter 132, having a lumen, can be used for insertion into a vessel. The catheter includes an insulated coating 134, having an exposed portion on the distal end. In operation, the exposed distal end may be positioned in the treatment site, adjacent to the plaque or particulate material to be fragmented. The catheter can be percutaneously or transcutaneously inserted into the vessel, wherein the distal end of the catheter is moved through the body of the patient to the treatment site. An external or partially implanted power source 138 is connected to the catheter, such that energy may be provided to the implantable medical device 12 from the distal end of the catheter. The released energy can take the form of radio frequency (RF), magnetic, electro magnetic (EM), acoustic, microwave, thermal, vibratory, optical laser, or heat energy, aiding in the fragmentation of particulate material or removal of plaque.

Figure 19:
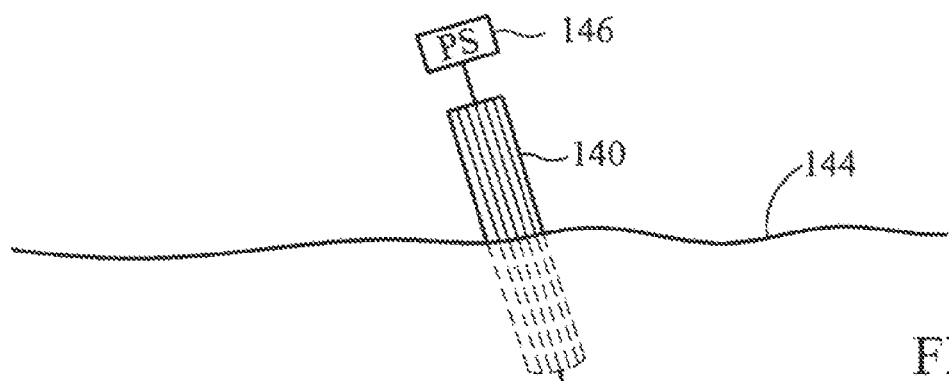
FIG. 19 depicts another embodiment of an implantable medical device of the present disclosure including an expandable cannula.
Figure 19:
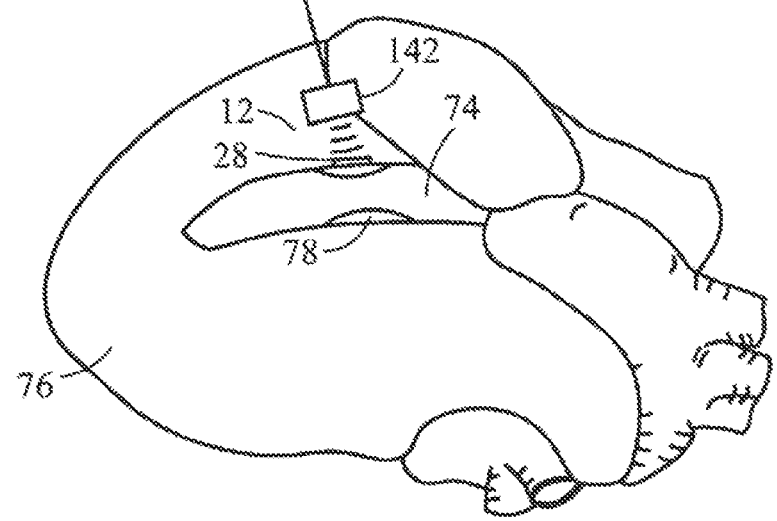

Referring to FIG. 19, in another embodiment an expandable cannula 140 may be used to position an energy transmission unit 142 in proximity to the medical device 12 of the present disclosure. Exemplary expandable cannulas are disclosed in U.S. Pat. No. 5,961,499, to Bonutti, and U.S. Pat. No. 5,431,676, to Dubrul et al., the contents of which are incorporated by reference. In one exemplary practical application of this embodiment, the implanted medical device 12 may be surgically positioned on or proximal to an outer surface of the aorta 74 of the heart 76. The implanted medical device 12 is positioned adjacent to a treatment site 78, an area of recurring clotting or stenotic area. The expandable cannula 140 is inserted through the skin 144 of the patient, until a tip portion is proximal to the implanted medical device 12. The expandable cannula 140 is expanded, increasing the diameter of the expandable cannula 140. The energy transmission unit 142 is positioned through the expandable cannula 140, in proximity to the implanted medical device 12. A power source ("PS") 146 provides energy to the energy transmission unit 142, activating the energy focusing device 28 of the implanted medical device 12. The energy focusing device 28 creates a convergent point shockwave focused from the implanted medical device 12, into the clot or stenotic area, breaking-up or fragmenting the clot or stenotic area.

Figure 20:
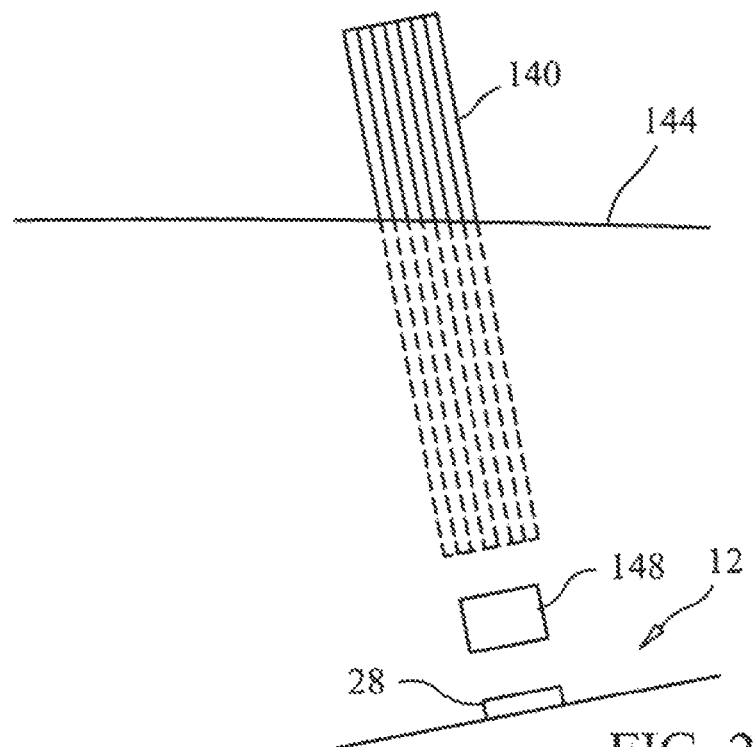
FIG. 20 depicts an internal energy unit of the present disclosure being inserted through an expandable cannula.

In the above embodiments, the present disclosure utilizes an external energy unit 10 or external power source 138 to provide energy to the implanted medical device 12. In an alternative embodiment shown in FIG. 20, an internal energy unit 148 unit may be surgical or percutaneously positioned proximal to the implanted medical device 12. Imaging techniques, such as MRI, CT scan, ultrasound, x-ray, fluoroscope, etc., may be used in the implantation of the internal energy unit 148 and medical device 12. An expandable cannula 140 may be used to position an internal energy unit 148 in proximity to the implantable medical device 12. The expandable cannula 140 is inserted through the skin 144 of the patient, until a tip portion is proximal to the implanted medical device 12. The expandable cannula 140 is expanded, increasing the diameter of the expandable cannula 140. The internal energy unit 148 is positioned through the expandable cannula 140, in proximity to the implanted medical device 12. The expandable cannula 140 is removed, and the insertion site sealed. The internal energy unit 148 is positioned to provide energy to the implanted medical device 12 to activate the energy focusing device 28.

The internal energy unit 148 includes a battery for providing power. If the battery has a limited life span, the internal energy unit 148 may be surgically or percutaneously removed and/or replaced. As described above, an expandable cannula 140 may be used to remove the internal energy unit 148. The expandable cannula 140 is inserted through the skin 144 of the patient, until a tip portion is proximal to the implanted medical device 12. The expandable cannula 140 is expanded, increasing the diameter of the expandable cannula 140. The internal energy unit 148 is removed through the expandable cannula 140. A replacement internal energy unit 148 may then be positioned through the expandable cannula 140, in proximity to the implanted medical device 12. The expandable cannula 140 is removed, and the insertion site sealed.

Alternatively, the internal energy unit 148 may include a rechargeable battery. As described above and in FIG. 12, the rechargeable battery 110 may be recharged by positioning an external energy unit 10 on the skin of the patient's body, aligned with the rechargeable battery 110. Energy is transmitted through the body of the patient to the rechargeable battery 110.

In the above embodiment, the rechargeable battery 110 is described as requiring an external energy unit 10 to be recharged. However it is contemplated, that the rechargeable battery 110 can include a self-recharging mechanism. The self-recharging mechanism utilizes the movement of the patient to generate power to recharge the rechargeable battery.

As described in FIG. 11, the internal energy unit 148 may include a control unit 100. In operation, the control unit 100 is configured to selectively activate the energy focusing device 28 at pre-programmed set time intervals. Alternatively, the implantable medical device 12 includes sensor assemblies 80. As set time intervals, the control unit 100 activates the sensor assemblies 80 to take data readings of the treatment site. In response to these measurements, if required, the control unit 100 may also selectively activate one or more energy focusing device(s) 28 to break-up or fragment particulate material. After an initial treatment with the energy focusing device(s) 28, the treatment site may be re-assessed to determine if further treatment is required. This process may be repeated until the treatment site is substantially free of particulate material, as may be determined by pre-set parameters programmed into control unit 100.

In the above examples, the present disclosure has been described as treating clotting and stenotic areas in the heart. However, it is contemplated that the present disclosure can be used on any organ, joint, or portion of the body requiring breaking or fragmenting of particulate material either alone, or in combination with drug delivery, tissue graft, or cell therapy. Additionally, the present disclosure can be used in conjunction with pharmaceutical treatment, which can result in a decrease in the dosage of the pharmaceutical or a decrease in the treatment period.

In an another exemplary practical application of an embodiment according to the present disclosure, the external energy units 10 may be used to prevent or treat the formation of deep vein thrombosis ("DVT"). The treatment may be done on a daily basis or an occasional basis, during surgery, during long period of inactivity, or as part of a post-operative treatment. For example, on long airplane flights, such as transatlantic or transpacific flights, passengers typically remain in a cramped seated position for extended periods of time, which can result in the formation of DVT. In this situation, the external energy units 10 may be positioned on a passenger, and used to prevent and/or treat DVT.

The treatment of DVT (particularly as part of a post-operative therapy) traditionally includes the application of pharmaceutical agents, such as anti-coagulants or blood thinners to prevent the formation and break-up clotting or plaque formations. For example, a treatment of 2-10 mg of warfain sodium, COUMADIN, may be required for 3-6 month. However, the use of such pharmaceutical agents have adverse side effects, including bleeding, infection, hemarthrosis, pain, and in extreme cases death.

Figure 21:
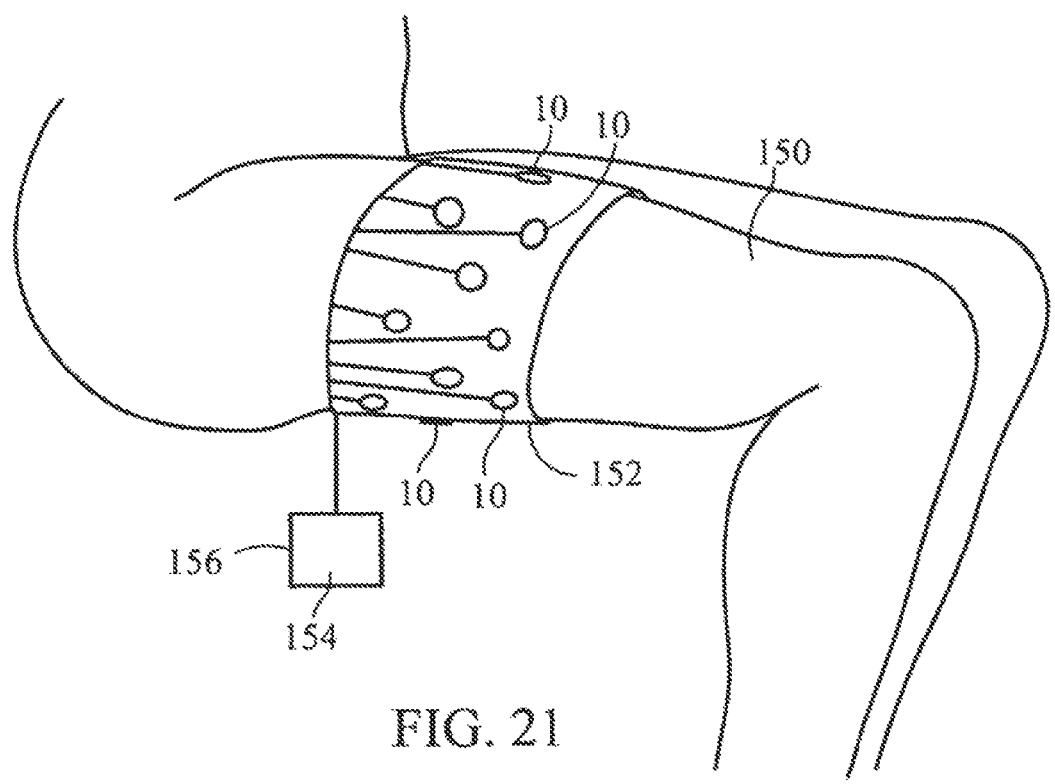
FIG. 21 depicts another embodiment of an energy system of the present disclosure including a sleeve.

The external energy units 10 of the present disclosure may be used in the prevention or treatment of DVT (either as an alternative or as an adjunct to drug treatment), having the additional beneficial effect of decreasing the use, the dosage and/or duration of the pharmaceutical agents. Referring to FIGS. 21 and 22, a plurality of external energy units 10 may be positioned about a patient, for example, a leg 150 of a patient. The external energy units 10 may be positioned on the skin of the leg 150 of the patient. Each of the external energy units 10 is operably connected to a power supply 154, including a controller unit 156 for selectively activating the individual external energy units 10. The external energy units 10 are configured to direct energy 158 into the leg 150 of the patient to breakup any type of thrombin or clot formation 160. When used in conjunction with the pharmaceutical agents, the external energy unit 10 may allow for a decrease in the dosage or duration of use of the pharmaceutical agents. This may result in a decrease in the occurrence and severity of the unwanted side effect of the pharmaceutical agents. In some instance, the external energy unit 10 may be used in lieu of the pharmaceutical agent, removing the occurrence of the unwanted side effects.

The controller unit 156 may selectively activate the external energy units 10 in a continuous sequence or in a pulsating sequence. A pulsating sequence produces a pulsed energy 158 directed into the leg 150 of the patient. The directed energy 158 can include, but not be limited to, ultrasonic, vibratory, microwave, RF, EM, ESW, or other types of energy, in a pulsed monomodal, and/or multimodal form.

The external energy units 10 may be removable attached to the leg 150 of the patient using an adhesive material. For example, each of the energy units 10 may include an adhesive backing for affixation to the leg 150 of the patient. The adhesive backing allows the energy units 10 to be each attached to and removed from the leg 150 of the patient.

Alternatively, the external energy units 10 may be integrated into an appliance 152 fitted about the leg 150 of the patient, positioning the external energy units 10. The appliance 152 may take the form of an elastic sleeve, wherein the elastic sleeve provides a continual pressure about the leg 150 of the patent. Alternatively, the appliance 152 may be a compressive stocking, TED hose, tourniquet, pulsatile stocking, or other graduated compressive device.

In an embodiment, the appliance 152 may be a pulsatile stocking. A pulsatile stocking is used to applying compressive pressure to the leg 150 of the patient. The pulsatile stocking provides intermittent pulses of compressed air which sequentially inflate multiple chambers in the stocking, resulting in a wave-like milking action which forcibly assists blood flow through the veins and results in greatly increased peak blood flow velocity. The pulsatile stocking is configured to be slidably positionable about the leg 150 of the patient, allowing for optimal positioning of the external energy units 10 for treatment.

The external energy units 10 are integrated to the pulsatile stocking and may be used in conjunction with the wave-like milking action of pulsatile stocking to breakup or prevent any type of thrombin or clot formation 160. As the intermittent pulses of compressed air sequentially inflate multiple chambers in the pulsatile stocking, the controller unit 156 activates the energy units 10, directing energy 158 into the leg 150. The controller unit 156 may selectively activate the external energy units 10 in a continuous sequence or in a pulsating sequence producing a pulsed energy 158. The combination of the wave-like milking action of the pulsatile stocking and directed energy 158 from the external energy units 10 work in unison to prevent the formation of and break-up clotting or plaque formations 160.

Referring to FIGS. 21 and 23, implanted medical devices 12 of the present disclosure can be surgically positioned on and about a vessel 162, for example in the leg 150, at locations of reoccurring clotting 160. As discussed above, implantable medical device 12 may include energy focusing device(s) 28 which may be activated by the external energy units 10. The plurality of external energy units 10 are positioned on the leg 150 of the patient and at least some of the external energy units 10 are aligned with implanted medical devices 12. At set time intervals, external energy units 10 may be selectively activated, activating the correspondingly aligned energy focusing devices 28. The external energy units 10 and energy focusing devices 28 are positioned such that pulsed energy may be selectively directed into the leg of the patient to fragment/prevent clotting or plaque formations.

As noted above, the external energy units 10 may be integrated into an appliance 152 which is fitted about the leg 150 of the patient. The appliance 152 may be a compressive stocking, TED hose, tourniquet, pulsatile stocking, or other graduated compressive device. For example, when the appliance 152 is a pulsatile stocking, the external energy units 10 may selectively activate correspondingly aligned energy focusing devices 28 which work in conjunction with the wave action of the pulsatile stocking.

Referring to FIG. 24, in another embodiment a pulsatile stocking 170 can be used in conjunction with the appliance 152 of FIG. 19. The pulsatile stocking 170 is used to applying compressive pressure to a lower portion of the leg 150 of the patient. The pulsatile stocking 170 provides intermittent pulses of compressed air which sequentially inflate multiple chambers in the sleeve 170, resulting in a wave-like milking action which forcibly assists blood flow through the veins and results in greatly increased peak blood flow velocity. The pulsatile stocking 170 is configured to be slidably positionable on the lower portion of the leg 150 of the patient, allowing for optimal positioning for treatment. Alternatively, a compressive stocking, TED hose, tourniquet, or other graduated compressive device fitted about the leg 150 of the patient can be used.

In the above examples, the appliance 152 or pulsatile stock 170 is described as fitting over the leg portion of the patient. However, it is contemplated that the appliance 170 or pulsatile stocking 152 can be fitted over any portion of the body of the patent. It is also contemplated that an appliance and pulsatile device can be fitted over the trunk or pelvic portion of the body of the patient. For example, the appliance can take the form of a mast compression stocking, which can be fitted about the trunk, thigh, and limbs of the patient. Similarly, the appliance or pulsatile device can be fitted about the trunk of the patient, for use after spinal or pelvic surgery.

Figure 25:
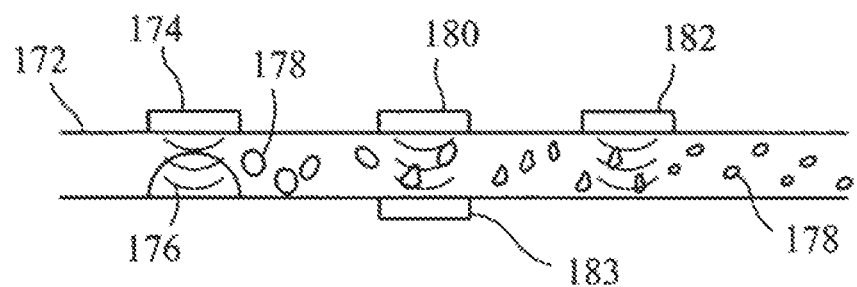
FIG. 25 depicts another embodiment of an implantable medical device of the present disclosure including downstream energy focusing devices.

Referring to FIG. 25, in an embodiment the implanted medical devices 12 of the present disclosure are surgically positioned along and about a vein, artery, or other vessel 172. As discussed above, implantable medical device 12 may include energy focusing device(s) 28 which may be activated by the external energy units 10. A first energy focusing device 174 is positioned proximal to a treatment site 176. The first energy focusing device 174 may selectively direct a convergent shockwave into the treatment site 176 to break-up or fragment the particulate material 178. Additional energy focusing devices 180 and 182 are positioned downstream of the treatment site, directing convergent shockwaves into the vessel 172.

As the broken-up or fragmented particulate material 178 travels from the treatment site 176 downstream, through the vessel 172, it will pass through the convergent shockwaves. The convergent shockwaves, further break-up or fragment the particulate material 178. The broken-up or fragmented particulate material 178 is decreased in size, such that the particulate material can be safely passed through the body, eliminating the need for the use of a filtering device, such as GREENFIELD filter.

A sensor assembly 183 can be further included. The sensor assembly 183 may be used to detect the fragmented particulate material 178 traveling through the vessel 172 and activate the down stream energy focusing devices 180 and 182 to further break-up fragmented particulate material 178.

Figure 26:
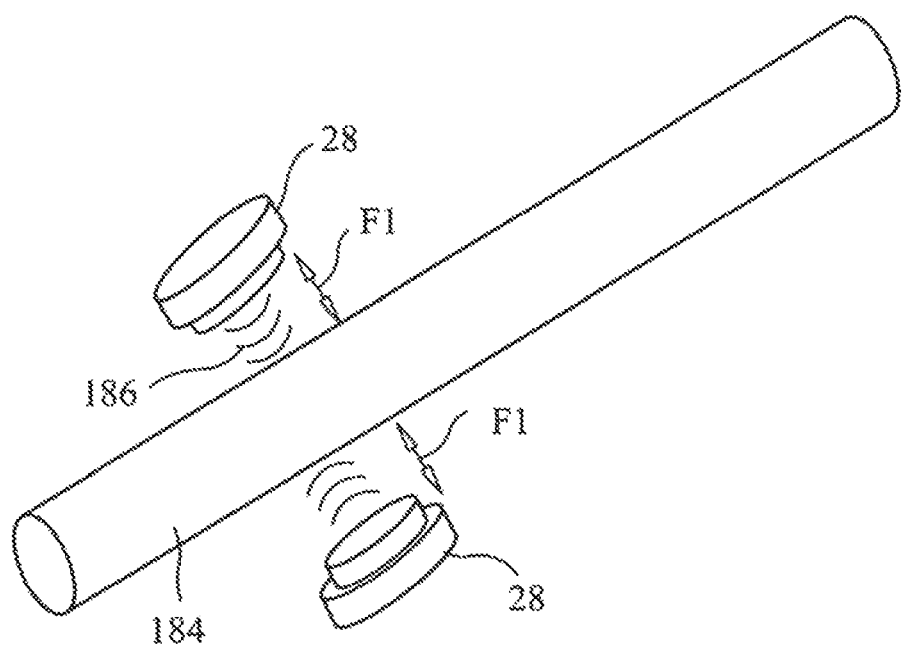
FIG. 26 depicts the implanted medical device of the present disclosure being utilized on small diameter veins.

Referring to FIG. 26, the energy focusing device(s) 28 of the present disclosure may be positioned in the body of the patient a distance F1 from the treatment site 184. The distance F1 is selected such that the convergent shockwave 186 is focused into the treatment site 184. When used to break-up or fragment particulate material in a small vessel, the diameter and surface area of the vessel may be insufficient to accommodate the energy focusing device(s) 28 or permit the convergent shockwave 186 to be located at the treatment site 184 (e.g. with the lumen of the vessel). The energy focusing device(s) 28 may be positioned proximal to the vein at a distance F1 from the treatment site 184, allowing the convergent shockwave 186 to be directed into the treatment site 184.

All references cited herein are expressly incorporated by reference in their entirety. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within scope and spirit of the present disclosure are to be included as further embodiments of the present disclosure. The scope of the present disclosure is accordingly defined as set forth in the appended claims.

What is claimed:

1. A system for treatment of Deep Vein Thrombosis (DVT), the system comprising:
    an appliance configured to secure to a portion of a body of a user, wherein the appliance is at least one of an elastic sleeve, compressive stocking, thrombo-embolic deterrent (TED) hose, tourniquet, and pulsatile stocking; and
    at least one external energy unit, positioned on the skin of the user and coupled to the appliance, that directs energy inside the body of the user to break-up or prevent at least one of thrombin or a clot formation and increase vascular flow, wherein the energy is acoustic energy in the range of 20 KHZ to 50 MHZ.

2. The system for treatment of DVT set forth in claim 1, wherein the appliance is configured to apply a compressive force to a leg of the user.

3. The system for treatment of DVT set forth in claim 1, wherein the appliance includes a chamber and the appliance is configured to provide compressed air into the chamber.

4. The system for treatment of DVT set forth in claim 1, further comprising at least one second external energy unit that directs energy inside the body of the user to at least one of break-up and prevent at least one of thrombin or a clot formation by directed energy that is at least one of a radio frequency, magnetic, electromagnetic, acoustic, microwave, thermal, vibratory, radiation, and extracorporeal shockwave energy, wherein a controller unit may selectively activate different types of external energy units.

5. The system for treatment of DVT set forth in claim 1, further comprising a controller unit that is configured to control the energy of the at least one energy unit.

* * * * *